US007014645B2

(12) United States Patent
Greene, Jr. et al.

(10) Patent No.: US 7,014,645 B2
(45) Date of Patent: *Mar. 21, 2006

(54) METHOD OF MANUFACTURING EXPANSILE FILAMENTOUS EMBOLIZATION DEVICES

(75) Inventors: George R. Greene, Jr., Costa Mesa, CA (US); Gregory M. Cruise, Rancho Santa Margarita, CA (US); Michael Constant, Mission Viejo, CA (US); Brian J. Cox, Laguna Niguel, CA (US); Terrance Tran, Westminster, CA (US)

(73) Assignee: Microvention Inc., Aliso Viejo, CA (US)

( * ) Notice: Subject to any disclaimer, the term of this patent is extended or adjusted under 35 U.S.C. 154(b) by 290 days.

This patent is subject to a terminal disclaimer.

(21) Appl. No.: 10/157,621

(22) Filed: May 29, 2002

(65) Prior Publication Data

US 2002/0177855 A1    Nov. 28, 2002

Related U.S. Application Data

(63) Continuation-in-part of application No. 09/867,340, filed on May 29, 2001, now Pat. No. 6,602,261, which is a continuation-in-part of application No. 09/542,145, filed on Apr. 4, 2000, now Pat. No. 6,299,619, which is a continuation-in-part of application No. 09/410,970, filed on Oct. 4, 1999, now Pat. No. 6,238,403.

(51) Int. Cl.
*A61B 17/08* (2006.01)

(52) U.S. Cl. .................................................. 606/158

(58) Field of Classification Search ............... 606/108, 606/158, 191, 194, 195, 200
See application file for complete search history.

(56) References Cited

U.S. PATENT DOCUMENTS 3,709,842 A    1/1973   Stoy et al.
(Continued)

FOREIGN PATENT DOCUMENTS

DE    196 47 280 A1    10/1997
(Continued)

OTHER PUBLICATIONS

Chirila, Traian V. et al.; "Poly(2-hydroyethyl methacrylate) sponges as implant . . . " Biomaterials 1993 vol. 14, No. 1.
(Continued)

*Primary Examiner*—Eduardo C. Robert
(74) *Attorney, Agent, or Firm*—Klein, O'Neill & Singh, LLP; Howard J. Klein

(57) ABSTRACT

An embolization device for occluding a body cavity includes one or more elongated, expansible, hydrophilic embolizing elements non-releasably carried along the length of an elongated filamentous carrier that is preferably made of a very thin, highly flexible filament or microcoil of nickel/titanium alloy. At least one expansile embolizing element is non-releasably attached to the carrier. A first embodiment includes a plurality of embolizing elements fixed to the carrier at spaced-apart intervals along its length. In second, third and fourth embodiments, an elongate, continuous, coaxial embolizing element is non-releasably fixed to the exterior surface of the carrier, extending along a substantial portion of the length of the carrier proximally from a distal tip, and optionally includes a lumenal reservoir for delivery of therapeutic agents. Exemplary methods for making these devices include skewering and molding the embolizing elements. In any of the embodiments, the embolizing elements may be made of a hydrophilic, macro-porous, polymeric, hydrogel foam material. In the second, third and fourth embodiments, the elongate embolizing element is preferably made of a porous, environmentally-sensitive, expansile hydrogel, which can optionally be made biodegradable and/or bioresorbable, having a rate of expansion that changes in response to a change in an environmental parameter, such as the pH or temperature of the environment.

12 Claims, 13 Drawing Sheets

U.S. PATENT DOCUMENTS

| | | | |
|---|---|---|---|
| 4,301,803 | A | 11/1981 | Handa et al. |
| 4,365,621 | A | 12/1982 | Brundin |
| 4,402,319 | A | 9/1983 | Handa et al. |
| 4,509,504 | A | 4/1985 | Brundin |
| 4,529,739 | A | 7/1985 | Scott et al. |
| 4,663,358 | A | 5/1987 | Hyon et al. |
| 4,994,069 | A | 2/1991 | Ritchart et al. |
| 5,120,349 | A | 6/1992 | Stewart et al. |
| 5,122,136 | A | 6/1992 | Guglielmi et al. |
| 5,129,180 | A | 7/1992 | Stewart |
| 5,226,911 | A | 7/1993 | Chee et al. |
| 5,250,071 | A | 10/1993 | Palermo |
| 5,258,042 | A | 11/1993 | Mehta |
| 5,304,194 | A | 4/1994 | Chee et al. |
| 5,312,415 | A | 5/1994 | Palermo |
| 5,320,639 | A | 6/1994 | Rudnick |
| 5,350,397 | A | 9/1994 | Palermo et al. |
| 5,354,290 | A | 10/1994 | Gross |
| 5,382,259 | A | 1/1995 | Phelps et al. |
| 5,456,693 | A | 10/1995 | Conston et al. |
| 5,476,472 | A | 12/1995 | Dormandy, Jr. et al. |
| 5,522,822 | A | 6/1996 | Phelps et al. |
| 5,536,274 | A | 7/1996 | Neuss |
| 5,541,234 | A | 7/1996 | Unger et al. |
| 5,549,624 | A | 8/1996 | Mirigian et al. |
| 5,573,994 | A | 11/1996 | Kabra et al. |
| 5,582,619 | A | 12/1996 | Ken |
| 5,624,461 | A | 4/1997 | Mariant |
| 5,624,685 | A | 4/1997 | Takahashi et al. |
| 5,645,558 | A | 7/1997 | Horton |
| 5,690,667 | A | 11/1997 | Gia |
| 5,690,671 | A | 11/1997 | McGurk et al. |
| 5,695,480 | A | 12/1997 | Evans et al. |
| 5,718,711 | A | 2/1998 | Berenstein et al. |
| 5,749,894 | A | 5/1998 | Engelson |
| 5,750,585 | A | 5/1998 | Park et al. |
| 5,752,974 | A | 5/1998 | Rhee et al. |
| 5,766,160 | A | 6/1998 | Samson et al. |
| 5,766,219 | A | 6/1998 | Horton |
| 5,797,953 | A | 8/1998 | Tekulve |
| 5,823,198 | A | 10/1998 | Jones et al. |
| 5,833,705 | A | 11/1998 | Ken et al. |
| 5,843,118 | A | 12/1998 | Sepetka et al. |
| 5,853,418 | A | 12/1998 | Ken et al. |
| 5,891,155 | A | 4/1999 | Irie |
| 5,891,192 | A | 4/1999 | Murayama et al. |
| 5,895,411 | A | 4/1999 | Irie |
| 5,911,717 | A | 6/1999 | Jacobson et al. |
| 5,911,731 | A | 6/1999 | Pham et al. |
| 5,916,235 | A | 6/1999 | Guglielmi |
| 5,935,145 | A | 8/1999 | Villar et al. |
| 5,935,148 | A | 8/1999 | Villar et al. |
| 5,976,162 | A | 11/1999 | Doan et al. |
| 5,980,514 | A | 11/1999 | Kupiecki et al. |
| 5,980,554 | A | 11/1999 | Lenker et al. |
| 6,004,338 | A | 12/1999 | Ken et al. |
| 6,013,084 | A | 1/2000 | Ken et al. |
| 6,015,424 | A | 1/2000 | Rosenbluth et al. |
| 6,024,754 | A | 2/2000 | Engelson |
| 6,093,199 | A | 7/2000 | Brown et al. |
| 6,113,629 | A | 9/2000 | Ken |
| 6,139,520 | A | 10/2000 | McCrory et al. |
| 6,143,007 | A | 11/2000 | Mariant et al. |
| 6,165,193 | A | 12/2000 | Greene et al. |
| 6,187,024 | B1 | 2/2001 | Boock et al. |
| 6,187,027 | B1 | 2/2001 | Mariant et al. |
| 6,193,728 | B1 | 2/2001 | Ken et al. |
| 6,245,090 | B1 | 6/2001 | Gilson et al. |
| 6,280,457 | B1 | 8/2001 | Wallace et al. |
| 6,296,632 | B1 | 10/2001 | Luscher et al. |
| 6,299,619 | B1 | 10/2001 | Greene, Jr. et al. |
| 6,312,421 | B1 | 11/2001 | Boock |
| 6,530,934 | B1 | 3/2003 | Jacobson et al. |
| 2001/0023325 | A1 | 9/2001 | Ferrera |
| 2001/0046518 | A1 | 11/2001 | Sawhney |

FOREIGN PATENT DOCUMENTS

| | | |
|---|---|---|
| WO | WO 81/01515 A1 | 6/1981 |
| WO | WO 97/48351 | 12/1997 |
| WO | WO 97/48351 A1 | 12/1997 |
| WO | WO 99/23954 | 5/1999 |
| WO | WO 99/23954 A1 | 5/1999 |
| WO | WO 99/56783 | 11/1999 |
| WO | WO 99/56783 A1 | 11/1999 |
| WO | WO 99/59479 | 11/1999 |
| WO | WO 99/59479 A1 | 11/1999 |
| WO | WO 99/65401 | 12/1999 |
| WO | WO 99/65401 A1 | 12/1999 |
| WO | WO 00/74577 A1 | 12/2000 |
| WO | WO 01/06950 A2 | 2/2001 |
| WO | WO 01/39811 A1 | 6/2001 |
| WO | 02/05731 A1 | 1/2002 |

OTHER PUBLICATIONS

Dawson, Robert C. et al; "Treatment of Experimental Aneurysms . . . " Neurosurgery, vol. 36, No. 1, Jan. 1995.

Edelman, Elazer R. et al.; "Controlled and <odulated Released of basic . . . " Biomaterials 1991. vol. 12 Sep.

Hoekstra, Djoed et al.; "Hyaluronan-Modified Surfaces for Medical Devices" Medical Device & Diagnostic Industry Feb. 1999.

Hogg, Phillip J. et al.;"INteraction of Platelet-derived growth . . . " Biochem Journal (1997) 326, 709-716 (printed in Great Britian).

Horak Daniel et al.;"Hydrogels in endovascualr embolization. II . . . " Biomaterials 1986, vol. 7 Nov.

Horak, D. et al;"New Radiopague polyHEMA-based . . . " JOurnal of Biomedical Materials Research vol. 34, 183-188 (1997).

Kim, Tay Sung et al.;"An experimental Study on Thrombogenicity . . . " Investigative Radiology, vol. 33, No. 7 1998 pp. 407-410.

Kwan, eddie S.K. et al.:"Endovascular Packing of Carotid . . . " AJNR 14:323-333, Mar./Apr. 1993.

Larsen, Nancy E. et al.;"Hylan get composition for percutaneous embolization . . . " Journal of Biomedical Materials Research, vol. 25, 699-710 (1991).

Latchaw, Richard E. et al.; "Polyvinyl Foam Embolization . . . " Radiology 131: 669-679, Jun. 1979.

Shimozuru, T. et al.; "Hydroxyapatite Coating of Detachable . . . " Interventional Neuroradiology 7 (Suppl 1):105-110, 2001.

Soranzo, C. et al.;"Evaluation of Two Hyaluronan Derivatives . . . " The 20th Annual Metting of the Society for Biomaterials Apr. 5-9, 1994, Boston Massachusetts, USA.

Tadavarthry, S. Murphy et al.; "Polyvinyl Alcohol (IVALON)—A New Embolic Material"Department of Radiology University of Minnesota Hospitals vol.,125, No. 3.

Woerly, S. et al.; "Intracerbral Implantation of Hydrogel-Coupled . . . "Journal of Neural Transplantation & Plasticity, vol. 5, No. 4, 1995, pp. 245-255.

Zollikofer, Christoph et al.;"A Combination of Stainkess Steel Coil and Compressed Ivalon: . . . "Radiology 138: 229-231, Jan. 1981.

Zollikoger, Christoph et al.:"Therapeutic Blockade of Arteries Using Compressed Ivalon" Department of Radiology University of Minnesota Hospitals, Radiology 136:635-640, Sep. 1980.

Ahuja, Arvin A, et al; "Platnium Coil Coatings ti Increase . . . " AJNR 14:794-798, Jul./Aug. 1993.

Dawson, Robert C. et al. "Treatment of Experimental Aneurysms Using Collagen-coated Microcoils" Nearosurgery vol. 36, No. 1, Jan. 1995.

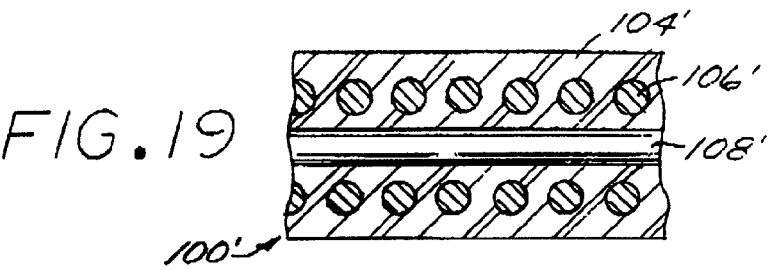
FIG. 19
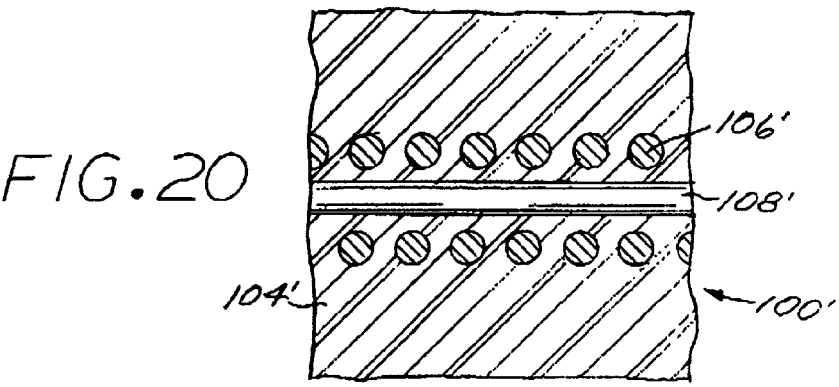
FIG. 20
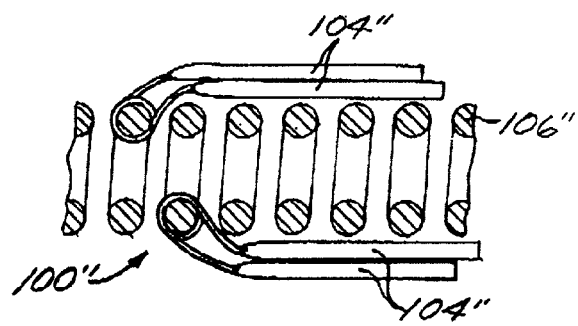
FIG. 21
FIG. 23
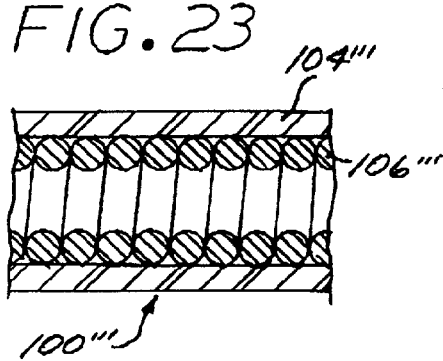
FIG. 22
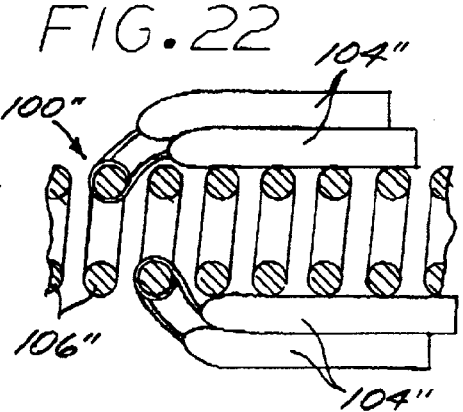

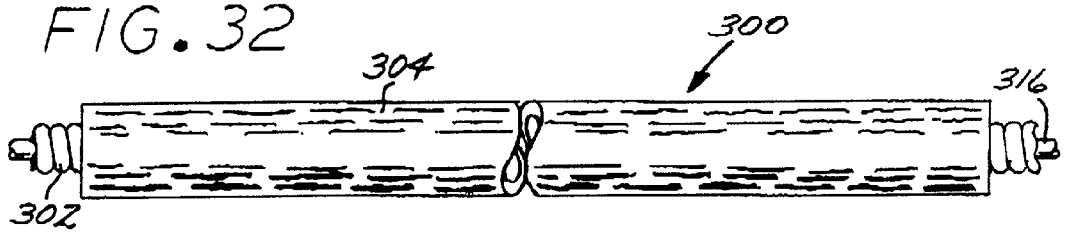
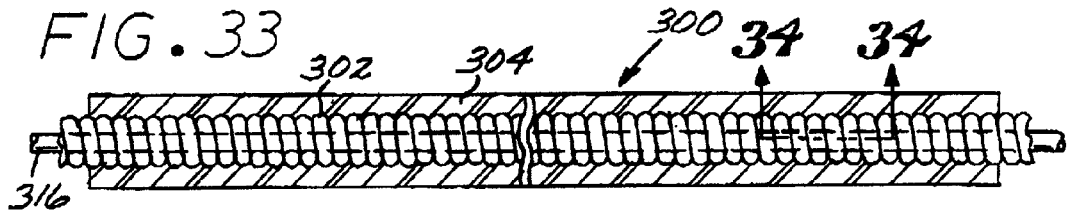
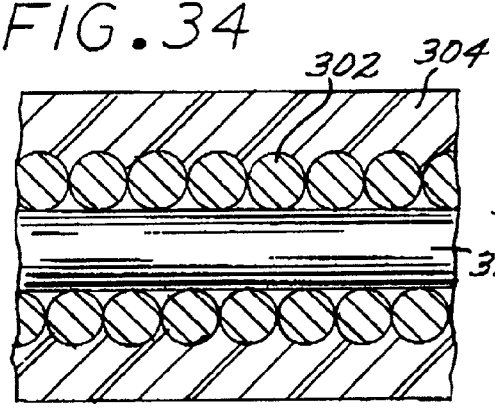
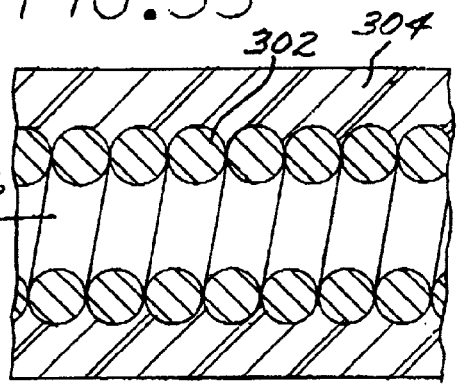
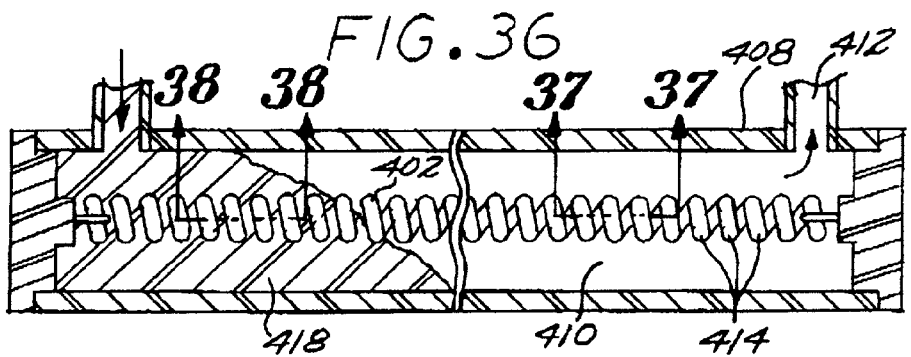

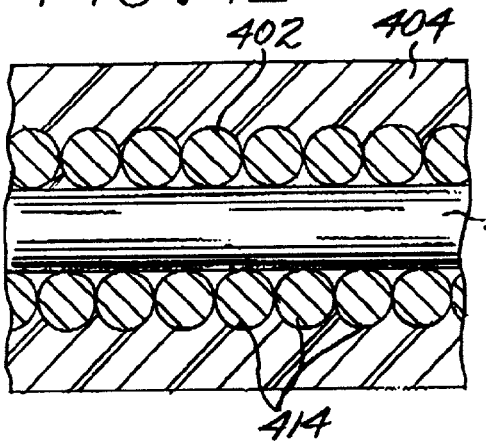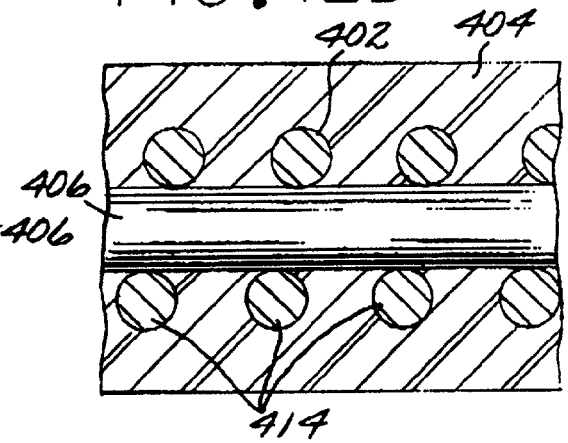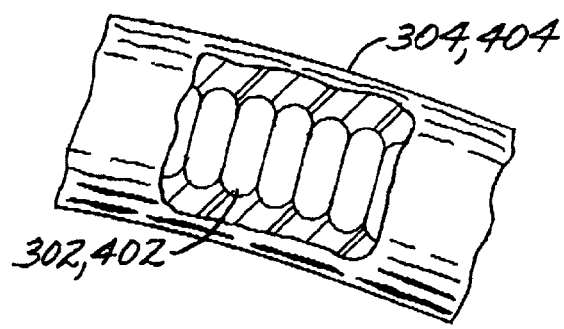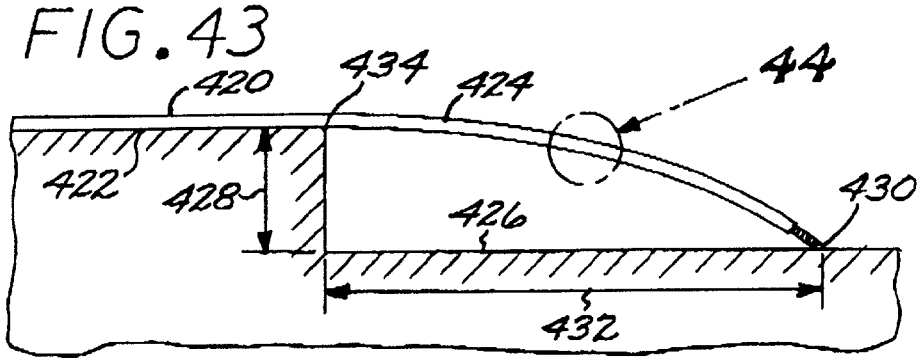

METHOD OF MANUFACTURING EXPANSILE FILAMENTOUS EMBOLIZATION DEVICES

CROSS REFERENCE TO RELATED APPLICATIONS

This application is a Continuation-in-Part of application Ser. No. 09/867,340, filed May 29, 2001, now U.S. Pat. No. 6,602,261, issued Aug. 5, 2003, which is a Continuation-in-Part of application Ser. No. 09/542,145, filed Apr. 4, 2000, now U.S. Pat. No. 6,299,619, issued Oct. 9, 2001, which is a Continuation-in-Part of application Ser. No. 09/410,970, filed Oct. 4, 1999, now U.S. Pat. No. 6,238,403, issued May 29, 2001.

FEDERALLY SPONSORED RESEARCH OR DEVELOPMENT

Not Applicable

BACKGROUND OF THE INVENTION

The present invention relates to devices for the occlusion of body cavities, such as in the embolization of vascular aneurysms and the like, and methods for making and using such devices. More specifically, the present invention relates to a device that is inserted into a body cavity, such as an aneurysm, to occlude the cavity by creating an embolism therein, a method for making the device, and a method for embolizing a body cavity using the device.

The occlusion of body cavities, blood vessels and other lumina by embolization is desired in a number of clinical situations. For example, the occlusion of fallopian tubes for the purposes of sterilization, and the occlusive repair of cardiac defects, such as a patent foramen ovale, patent ductus arteriosis, and left atrial appendage and atrial septal defects. The function of an occlusion device in such situations is to substantially block the flow of body fluids into or through the cavity, lumen, vessel, space or defect for the therapeutic benefit of the patient.

Vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been employed in the prior art. U.S. Pat. No. 4,819,637—Dormandy, Jr. et al., for example, describes a vascular embolization system that employs a detachable balloon delivered to the aneurysm site by an intravascular catheter. The balloon is carried into the aneurysm at the tip of the catheter, and is inflated inside the aneurysm with a solidifying fluid (typically a polymerizable resin or gel) to occlude the aneurysm. The balloon is then detached from the catheter by gentle traction on the catheter. While the balloon-type embolization device can provide an effective occlusion of many types of aneurysms or other body cavities, it is difficult to retrieve or move after the solidifying fluid sets, and it is difficult to visualize unless it is filled with a contrast material. Furthermore, there are risks of balloon rupture during inflation and of premature detachment of the balloon from the catheter.

Another approach is the direct injection of a liquid polymer embolic agent into the cavity or vascular site to be occluded. One type of liquid polymer used in the direct injection technique is a rapidly polymerizing liquid, such as a cyanoacrylate resin, particularly isobutyl cyanoacrylate, that is delivered to the target site as a liquid, and then is polymerized in situ. Alternatively, a liquid polymer that is precipitated at the target site from a carrier solution has been used. An example of this type of embolic agent is a cellulose acetate polymer mixed with bismuth trioxide and dissolved in dimethyl sulfoxide (DMSO). Another type is ethylene vinyl alcohol dissolved in DMSO. On contact with blood, the DMSO diffuses out, and the polymer precipitates out and rapidly hardens into an embolic mass that conforms to the shape of the aneurysm. Other examples of materials used in this "direct injection" method are disclosed in the following U.S. Pat. No. 4,551,132—Pasztor et al.; U.S. Pat. No. 4,795,741—Leshchiner et al.; U.S. Pat. No. 5,525,334—Ito et al.; and U.S. Pat. No. 5,580,568—Greff et al.

The direct injection of liquid polymer embolic agents has proven difficult in practice. For example, migration of the polymeric material from the aneurysm and into the adjacent blood vessel has presented a problem. In addition, visualization of the embolization material requires that a contrasting agent be mixed with it, and selecting embolization materials and contrasting agents that are mutually compatible may result in performance compromises that are less than optimal. Furthermore, precise control of the deployment of the polymeric embolization material is difficult, leading to the risk of improper placement and/or premature solidification of the material. Moreover, once the embolization material is deployed and solidified, it is difficult to move or retrieve.

Another approach that has shown promise is the use of thrombogenic microcoils. These microcoils may be made of a biocompatible metal alloy (typically, platinum and tungsten) or a suitable polymer. If made of metal, the coil may be provided with Dacron fibers to increase thrombogenicity. The coil is deployed through a microcatheter to the vascular site. Examples of microcoils are disclosed in the following U.S. Pat. No. 4,994,069—Ritchart et al.; U.S. Pat. No. 5,133,731—Butler et al.; U.S. Pat. No. 5,226,911—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,645,558—Horton; U.S. Pat. No. 5,658,308—Snyder; and U.S. Pat. No. 5,718,711—Berenstein et al.

The microcoil approach has met with some success in treating small aneurysms with narrow necks, but the coil must be tightly packed into the aneurysm to avoid shifting that can lead to recanalization. Microcoils have been less successful in the treatment of larger aneurysms, especially those with relatively wide necks. A disadvantage of microcoils is that they are not easily retrievable; if a coil migrates out of the aneurysm, a second procedure to retrieve it and move it back into place is necessary. Furthermore, complete packing of an aneurysm using microcoils can be difficult to achieve in practice.

A specific type of microcoil that has achieved a measure of success is the Guglielmi Detachable Coil ("GDC"), described in U.S. Pat. No. 5,122,136—Guglielmi et al. The GDC employs a platinum wire coil fixed to a stainless steel delivery wire by a solder connection. After the coil is placed inside an aneurysm, an electrical current is applied to the delivery wire, which electrolytically disintegrates the solder junction, thereby detaching the coil from the delivery wire. The application of the current also creates a positive electrical charge on the coil, which attracts negatively-charged blood cells, platelets, and fibrinogen, thereby increasing the thrombogenicity of the coil. Several coils of different diameters and lengths can be packed into an aneurysm until the aneurysm is completely filled. The coils thus create and hold a thrombus within the aneurysm, inhibiting its displacement and its fragmentation.

The advantages of the GDC procedure are the ability to withdraw and relocate the coil if it migrates from its desired location, and the enhanced ability to promote the formation of a stable thrombus within the aneurysm. Nevertheless, as in conventional microcoil techniques, the successful use of the GDC procedure has been substantially limited to small aneurysms with narrow necks.

Still another approach to the embolization of an abnormal vascular site is the injection into the site of a biocompatible "hydrogel," such as poly (2-hydroxyethyl methacrylate) ("pHEMA" or "PHEMA"); or a polyvinyl alcohol foam ("PAF"). See, e.g., Horák et al., "Hydrogels in Endovascular Embolization. II. Clinical Use of Spherical Particles", *Biomaterials,* Vol. 7, pp. 467–470 (November, 1986); Rao et al., "Hydrolysed Microspheres from Cross-Linked Polymethyl Methacrylate", *J. Neuroradiol.,* Vol. 18, pp. 61–69 (1991); Latchaw et al., "Polyvinyl Foam Embolization of Vascular and Neoplastic Lesions of the Head, Neck, and Spine", *Radiology*, Vol. 131, pp. 669–679 (June, 1979). These materials are delivered as microparticles in a carrier fluid that is injected into the vascular site, a process that has proven difficult to control.

A further development has been the formulation of the hydrogel materials into a preformed implant or plug that is installed in the vascular site or other body cavity by means such as a microcatheter. See, e.g., U.S. Pat. No. 5,258,042—Mehta. These types of plugs or implants are primarily designed for obstructing blood flow through a tubular vessel or the neck of an aneurysm, and they are not easily adapted for precise implantation within a sac-shaped vascular structure, such as an aneurysm, so as to fill substantially the entire volume of the structure.

U.S. Pat. No. 5,823,198—Jones et al. discloses an expansible PVA foam plug that is delivered to the interior of an aneurysm at the end of a guidewire. The plug comprises a plurality of pellets or particles that expand into an open-celled structure upon exposure to the fluids within the aneurysm so as to embolize the aneurysm. The pellets are coated with a blood-soluble restraining agent to maintain them in a compressed state and attached to the guidewire until delivered to the aneurysm. Because there is no mechanical connection between the pellets and the guidewire (other than the relatively weak temporary bond provided by the restraining agent), however, premature release and migration of some of the pellets remains a possibility.

There has thus been a long-felt, but as yet unsatisfied need for a device for effective occlusive treatment of aneurysms and other body cavities, and a method that can substantially fill aneurysms and other body cavities of a large range of sizes, configurations, and neck widths with an occlusive and/or thrombogenic medium with a minimal risk of inadvertent tissue damage, aneurysm rupture or blood vessel wall damage. There has been a further need for such a method and device that also allow for the precise locational deployment of the medium, while also minimizing the potential for migration away from the target location. In addition, a method and device meeting these criteria should also be relatively easy to use in a clinical setting. Such ease of use, for example, should preferably include a provision for good visualization of the device during and after deployment in a body cavity, lumen or aneurysm.

SUMMARY OF THE INVENTION

Broadly, an embolization device, according to a first aspect of the present invention, comprises one or more expansible, hydrophilic embolizing elements non-releasably carried along the length of a filamentous carrier. In a first preferred embodiment, the carrier is a suitable length of very thin, highly flexible filament of nickel/titanium alloy (Nitinol). A plurality of embolizing elements are spaced along the length of the carrier and are separated from each other on the carrier by radiopaque spacers in the form of highly flexible microcoils made of platinum or platinum/tungsten alloy, as in the thrombogenic microcoils of the prior art, as described above.

In a second preferred embodiment, the carrier comprises a continuous length of highly flexible, hollow microcoil made of a biocompatible metal (preferably platinum or platinum/tungsten alloy), with an optional core in the form of a continuous length of thin, highly flexible metal wire, preferably of a shape memory metal alloy such as Nitinol. Alternatively, the carrier may be a suitable length of flexible wire, cable, braid, or other construction that yields the desired flexibility. The carrier is preferably made of a biocompatible metal so as to be visible by means of X-rays or other visualization techniques known in the art, but it also may be made of a suitable polymer that is visible (or is rendered visible) through any of the known visualization methods. The carrier should have sufficient column strength to allow the device to be pushed through a microcatheter.

In the second preferred embodiment, an elongate, continuous, coaxial embolizing element is non-releasably fixed to the exterior surface of the carrier, extending along a substantial portion of the length of the carrier proximally from a distal tip.

In a third exemplary embodiment of an embolization device, the carrier comprises an elongated, filamentous carrier, and the embolizing element comprises a coaxial member of an expansile, hydrophilic polymer, or hydrogel, encapsulating at least a portion of the carrier's length. In a variant incorporating a tubular carrier, such as an tubular braid or the flexible, hollow microcoil described above, the coaxial polymer member is formed such that the lumen of the carrier is substantially void of the polymer, thereby defining an axial reservoir in the carrier. The reservoir constitutes a chamber in which therapeutic agents, e.g., medications, can be placed for delivery to a patient via implantation of the device in a cavity in the patient's body.

A fourth exemplary embodiment of the embolization device is similar in most respects to the third embodiment described above, except that, in one possible variant thereof in which the carrier comprises a flexible tube, the hydrophilic polymer of the coaxial embolizing member encapsulating the carrier also substantially fills the lumen of the carrier, such that the entire surface of the encapsulated portion of the carrier is in contact with the polymer of the embolizing member and no reservoir is created in the carrier.

A first exemplary embodiment of a method for making the third embodiment of the embolization device comprises the provision of a softened, elongated embolizing member of hydrogel supported in a tubular holder. In one possible embodiment of the method, a stiff, elongated support mandrel is inserted coaxially in the lumen of a tubular carrier, such as a helical coil, to straighten and stiffen it, and the soft polymer member is then coaxially skewered with the carrier-and-mandrel, such that the polymer member coaxially encapsulates at least a portion of the length of the carrier.

The skewered polymer member is then ejected from the tubular holder and dehydrated in a hygroscopic bath, e.g., alcohol, to remove water from, and thereby shrink, the coaxial polymer embolizing member to a size suitable for passage through the lumen of a catheter.

After dehydration, the polymer member is treated, e.g., in an acid bath, to set the rate of hydration of the polymer, and hence, the rate of expansion of the member, in an aqueous environment, e.g., blood, in response to the level of a physical parameter of the environment, e.g., its temperature or pH level. After the hydration rate of the device is set, it is washed to remove any processing impurities, dried by heating, e.g., in an oven, and then packaged in a sterile container.

A second exemplary embodiment of a method for making the fourth embodiment of the embolization device comprises the provision of a mold having an elongated cavity therein. An elongated filamentous carrier, which may comprise a tubular carrier, as above, is disposed coaxially within the cavity of the mold. In one advantageous variant in which a tightly-coiled helical carrier is employed, the carrier is elastically stretched along its axis, such that the coils are held spaced apart from each other by the mold before disposition therein. In another possible variant, the coils of a helical carrier are formed permanently spaced apart, i.e., without being elastically stretched in the mold. In yet another possible variant, a mandrel is inserted in the lumen of a tubular carrier, in a manner similar to that described above in connection with the first method.

After the carrier is disposed coaxially within the cavity of the mold, a quantity of a softened, expansile, hydrophilic polymer is transferred into the mold under pressure, such that the polymer is molded by the cavity into an embolization member that coaxially encapsulates at least a portion of the length of the carrier. In those variants in which the carrier comprises a tubular carrier that is not internally supported by a lumenal mandrel, the polymer is also caused to flow into the lumen of the carrier, substantially filling it.

After the polymer member is molded onto the carrier, the device is released from the mold, which enables the adjacent coils of an elastically stretched helical carrier to spring back axially into contact with one another through the still-soft polymer member. In those variants incorporating a tubular carrier internally supported by a lumenal mandrel, the mandrel is removed to define a lumenal reservoir in the device for the disposition of therapeutic agents, as in the first exemplary method above. Indeed, the post-molding processes applied to the device are substantially the same as those applied to the device in the first method embodiment described above, including dehydration of the coaxial member, adjustment of its rate of hydration, and the washing, drying and packaging of the device.

The second exemplary method embodiment of the invention is thus capable of making substantially the same embodiments of the embolization device as are made by the first method embodiment, including those with an axial reservoir, as well as other variants of the device, including those having no axial reservoir, and in which the entire surface, including any internal surface, of the encapsulated portion of the carrier is in contact with the polymer of the expansile, coaxial embolizing member.

In both the first and second exemplary methods, the lumenal support mandrel can be removed from the carrier at any stage of the process after the skewered or molded coaxial member is ejected from the holder or mold and before the dried and finished device is packaged. Removal of the mandrel creates a lumenal reservoir in the carrier that, as described above, can be used as a reservoir for the delivery of therapeutic agents, e.g., medications, blood cells, and the like, to a patient via the device. Thus, one possible embodiment of a method for delivering a therapeutic agent to a patient may comprise making an embolization device having an axial reservoir in accordance with either the first or second exemplary methods, disposing a therapeutic agent in the reservoir of the device, and implanting the device in a body cavity of the patient.

Moreover, in both the third and fourth exemplary embodiments of the device, the flexibility, size, and lubricity of the hydrophilic polymer of the coaxial member, and hence, the device itself, all increase with the degree of hydration of the polymer. In accordance with one exemplary embodiment of this invention, the rate of hydration of the polymer in an aqueous environment is, as described above, set during manufacture to a specific value in response to a corresponding specific level of a physical parameter of the environment, e.g., its pH level.

Thus, in one possible embodiment of a method for preparing a fully dehydrated device for insertion into a body cavity via a catheter, the dry device is first immersed in an aqueous medium, e.g., a saline solution, having a relatively low pH level, such that the rate of hydration of the coaxial polymer member in the medium is correspondingly slow. This increases the flexibility and lubricity of the device such that it can be easily inserted into and moved through the lumen of the catheter and into the body cavity, but at a rate that is slow enough to afford the physician ample time to implant the device without allowing it to expand to a size that cannot be inserted into or moved easily through the catheter. However, once the device is emplaced in the cavity, its rate of hydration increases substantially in response to the increased pH level of the surrounding physiological aqueous environment, i.e., blood or plasma, such that the coaxial embolizing member of the device then expands correspondingly rapidly to occlude the cavity.

In yet other embodiments of the embolization device incorporating embolizing elements of hydrogel, the formulation of the polymer of the coaxial member can be modified to incorporate polymers that degrade, or break down, in the body after a period of time in response to, e.g., hydrolysis or enzymatic action, into simpler molecular constituents that can be absorbed by the patient's body and/or eliminated from it as waste. Thus, in another possible embodiment of the device incorporating a hydrogel embolizing member, the member can be made such that it is biodegradable and/or bioresorbable in the patient's body.

In either of the first two preferred embodiments, the embolizing elements may be made of a hydrophilic, macroporous, polymeric, hydrogel foam material, in particular a swellable foam matrix formed as a macroporous solid comprising a foam stabilizing agent and a polymer or copolymer of a free radical polymerizable hydrophilic olefin monomer cross-linked with up to about 10% by weight of a multiolefin-functional cross-linking agent. Such a material is described in U.S. Pat. No. 5,750,585—Park et al., the disclosure of which is incorporated herein by reference. The material may be modified, or provided with additives, to make the implant visible by conventional imaging techniques.

In the second, third and fourth preferred embodiments, the elongate coaxial embolizing element is preferably made of a porous, environmentally-sensitive, expansile hydrogel, of the type described in prior co-pending U.S. patent application Ser. No. 09/804,935, assigned to the assignee of this application and of the invention disclosed and claimed herein. application Ser. No. 09/804,935 (the disclosure of which is incorporated herein by reference) discloses hydrogels that experience an increase in lubricity and undergo controlled volumetric expansion at a rate that changes in response to changes in such environmental parameters as pH or temperature. These hydrogels are prepared by forming a liquid mixture that contains (a) at least one monomer and/or polymer, at least a portion of which is sensitive to changes in an environmental parameter; (b) a cross-linking agent; and (c) a polymerization initiator. If desired, a porosigen (e.g., NaCl, ice crystals, or sucrose) may be added to the mixture, and then removed from the resultant solid hydrogel to provide a hydrogel with sufficient porosity to permit cellular ingrowth.

The controlled rate of expansion is provided through the incorporation of ethylenically unsaturated monomers with ionizable functional groups (e.g., amines, carboxylic acids). For example, if acrylic acid is incorporated into the crosslinked network, the hydrogel is incubated in a low pH solution to protonate the carboxylic acids. After the excess low pH solution is rinsed away and the hydrogel dried, the hydrogel can be introduced through a microcatheter filled with saline at physiological pH or with blood. The hydrogel cannot expand until the carboxylic acid groups deprotonate. Conversely, if an amine-containing monomer is incorporated into the crosslinked network, the hydrogel is incubated in a high pH solution to deprotonate the amines. After the excess high pH solution is rinsed away and the hydrogel dried, the hydrogel can be introduced through a microcatheter filled with saline at physiological pH or with blood. The hydrogel cannot expand until the amine groups protonate.

Alternatively, in the second preferred embodiment, the elongate coaxial embolizing element may be in the form of a stretch-resistant outer layer applied to the exterior of the carrier along a substantial portion of the length of the carrier. The stretch-resistant outer layer is preferably formed of an expansile material, such as those described above, but it may also be formed of any stretch-resistant, biocompatible polymer, such as, for example, polyurethane, polyester, polytetrafluoroethylene (PTFE), nylon, polymethylmethacrylate (PMMA), and silicone.

A second aspect of the present invention is a method for embolizing a body cavity or a vascular site, comprising, in the preferred embodiment the steps of: (a) passing a microcatheter intravascularly so that its distal end is introduced into a target vascular site; (b) passing a vaso-occlusive device through the microcatheter into the target vascular site so that the vaso-occlusive device assumes a three-dimensional configuration that fills a portion of the volume of the target vascular site; (c) providing a vascular embolization device comprising at least one expansible embolizing element non-releasably connected to a filamentous carrier; (d) passing the embolization device through the microcatheter so that it emerges from the distal end of the microcatheter and into the target vascular site; and (e) expanding the embolizing element or elements in situ so that at least about 30%, and preferably more than about 40%, of the total the volume of the target vascular site is filled, while maintaining the connection between the embolizing element or elements and the carrier.

Preferably, the vaso-occlusive device is of the type that is initially in the form of an elongate, flexible, filamentous element for delivery through the microcatheter, and that assumes a three-dimensional geometry upon installation in the target vascular site. One such device is the above-described GDC (U.S. Pat. No. 5,122,136—Guglielmi et al., the disclosure of which is incorporated herein by reference).

Other such devices are described in, for example, U.S. Pat. No. 5,766,219—Horton; U.S. Pat. No. 5,690,671—McGurk et al.; and U.S. Pat. No. 5,911,731—Pham et al., the disclosure of which are incorporated herein by reference. Still other types of occlusive devices known in the art may also perform satisfactorily in this method.

In an alternative embodiment of the method of the present invention, the method comprises the steps of: (a) deploying an intravascular device to a position in a blood vessel adjacent to a target vascular site; (b) providing a vascular embolization device comprising at least one expansible embolizing element non-releasably connected to a filamentous carrier; (c) passing a microcatheter intravascularly so that the distal end of the microcatheter passes through the intravascular device into the target vascular site; (d) passing the embolization device through the microcatheter so that it emerges from the distal end of the microcatheter into the target vascular site; and (e) expanding the embolizing element or elements in situ substantially to fill the volume of the target vascular site while maintaining the connection between the embolizing element or elements and the carrier.

It is understood that the step of providing the embolization device may follow the step of passing the microcatheter intravascularly.

In this alternative embodiment of the method aspect of the present invention, the intravascular device may be of the type disclosed in U.S. Pat. No. 5,980,514—Kupiecki et al., the disclosure of which is incorporated herein by reference. This intravascular device comprises a filamentous element that is introduced by a microcatheter to the juncture of an aneurysm or the like, and that then assumes the configuration of a coil adjacent the neck of the aneurysm.

In some instances, the step of passing a vaso-occlusive device or an intravascular device through the microcatheter to the target vascular site may be omitted.

The embolization bodies or elements, in the preferred embodiment, have an initial configuration in the form of small, substantially cylindrical "micropellets" of small enough outside diameter to fit within the microcatheter. The bodies are hydrophilically expansible into an expanded configuration in which they substantially conform to and fill the vascular site.

The present invention provides a number of significant advantages. Specifically, the present invention provides an effective body cavity or vascular embolization device that can be deployed within a cavity or vascular site with excellent locational control, and with a lower risk of vascular rupture, tissue damage, or migration than with prior art devices. Furthermore, the embolization device effects a conformal fit within the site that promotes effective embolization, and yet its ability to be delivered to the site through a microcatheter facilitates precise and highly controllable deployment. In addition, the essentially filamentous initial configuration of the embolization device, whereby it readily conforms to the interior dimensions of the target site, allows it to be used effectively to embolize body cavities having a wide variety of sizes, configurations, and (in the particular case of aneurysms) neck widths. These and other advantages will be readily appreciated from the detailed description that follows.

BRIEF DESCRIPTION OF THE DRAWINGS

FIG. 19 is a partial axial cross-sectional view of a first modified form of an embolic device in accordance with the second preferred embodiment of the present invention, showing the device in its normal or non-expanded state;

FIG. 20 is a view similar to that of FIG. 19, showing the device of FIG. 19 in its expanded state after deployment in a vascular site;

FIG. 21 is a partial axial cross-sectional view of a second modified form of an embolic device in accordance with the second preferred embodiment of the present invention, showing the device in its normal or non-expanded state;

FIG. 22 is a view similar to that of FIG. 21, showing the device of FIG. 21 in its expanded state after deployment in a vascular site;

FIG. 23 is a detailed axial cross-sectional view of a third modified form of an embolic device in accordance with the second preferred embodiment of the present invention;

FIG. 32 is an elevational view of the finished embolization device in accordance with the third exemplary embodiment thereof, with the lumenal mandrel FIG. 26 remaining in place;

FIG. 33 is a cross-sectional elevation view of the embolization device of FIG. 32;

FIG. 34 is an enlarged, partial cross-sectional view into the embolization device of FIG. 33, as revealed by the section taken therein along the lines 34—34;

FIG. 35 is an enlarged partial cross-sectional view similar to that of FIG. 34, showing an axial reservoir defined in the embolization device by removal of the lumenal mandrel therefrom;

FIG. 36 is a cross-sectional elevation view of a fourth exemplary embodiment of an embolization device in accordance with the invention being molded in accordance with a second exemplary embodiment of a method for making the device in accordance with the invention;

FIG. 42A is an enlarged, partial cross-sectional view into the embolization device of FIG. 41, as revealed by the section taken therein along the lines 42—42, showing one possible variant thereof in which the coils of a helically coiled carrier are spaced close together and the lumenal mandrel is removed to define an axial reservoir in the carrier;

FIG. 42B is a view similar to that of FIG. 42A, showing another variant in which the coils of the carrier are spaced apart from each other;

FIG. 43 is schematic elevation view of a method and apparatus for measuring the flexibility of an embolization device; and, FIG. 44 is an enlarged, partial cross-sectional detail view of the embolization device being measured in FIG. 43, as revealed by the encircled detail 44 therein.

DETAILED DESCRIPTION OF THE INVENTION

The Embolization Device: First Preferred Embodiment.

Figure 1:
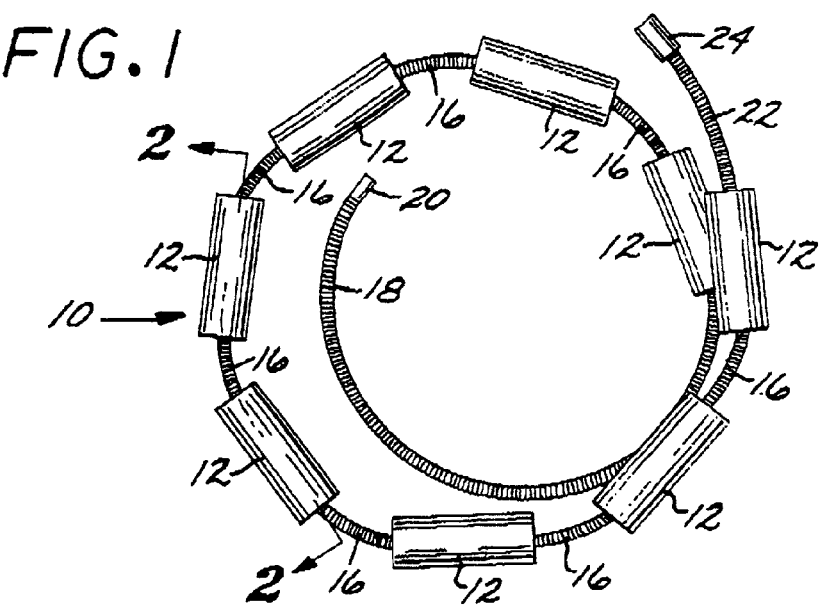
FIG. 1 is an elevational view of a vascular embolization device in accordance with a first preferred embodiment of the invention.
Figure 2:
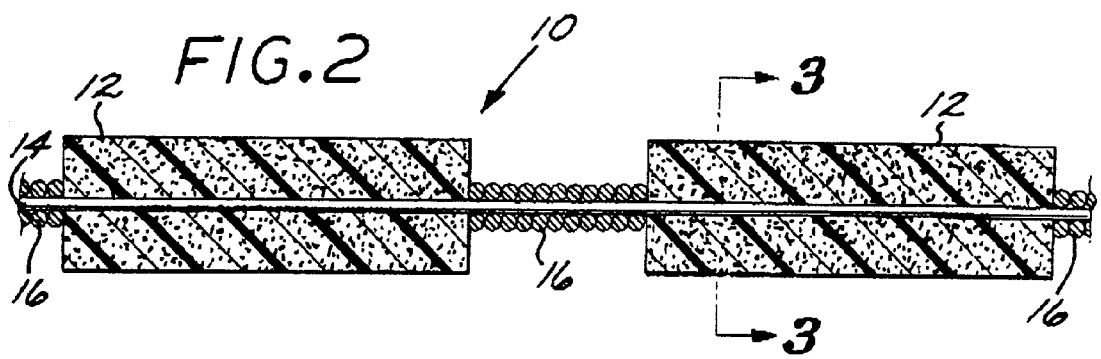
FIG. 2 is a cross-sectional view taken along line 2—2 of FIG. 1.
Figure 3:
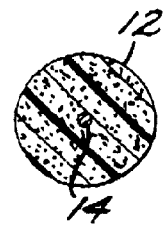
FIG. 3 is a cross-sectional view taken along line 3—3 of FIG. 2.

A vascular embolization device 10, in accordance with a first preferred embodiment of the present invention, is shown in FIGS. 1, 2 and 3. In the preferred embodiment, the embolization device 10 comprises a plurality of embolizing bodies, each configured as a substantially cylindrical "micropellet" 12, located at spaced intervals along a filamentous carrier 14. The number of micropellets 12 will vary, depending on the length of the carrier 14, which, turn, will depend on the size of the vascular site to be embolized. For a large vascular site, for example, eight to twelve micropellets may be used, although an even larger number may be used if necessary. In some applications (e.g., very small aneurysms), as few as one or two micropellets may be used.

Also carried on the carrier 14 is a plurality of highly flexible microcoil spacers 16, each of which is disposed between and separates a pair of micropellets 12. The carrier 14 has a distal portion on which is carried a relatively long distal microcoil segment 18 that is retained in place by a distal retention member 20. The carrier 14 has a proximal portion on which is carried a relatively long proximal microcoil segment 22. The proximal end of the device 10 is terminated by a hydrogel linkage element 24, to be described below. The spacers 16, the distal microcoil segment 18, and the proximal microcoil segment 22 are all highly flexible, and they are preferably made of platinum or platinum/tungsten wire, which has the advantages of being biocompatible and radiopaque. The micropellets 12 are non-releasably carried on the carrier 14. They may be fixed in place on the filamentous carrier 14, either mechanically or by a suitable biocompatible, water-insoluble adhesive, or they may be simply strung loosely on the carrier 14 between successive spacers 16.

The micropellets 12 are preferably formed of a biocompatible, macroporous, hydrophilic hydrogel foam material, in particular a water-swellable foam matrix formed as a macroporous solid comprising a foam stabilizing agent and a polymer or copolymer of a free radical polymerizable hydrophilic olefin monomer cross-linked with up to about 10% by weight of a multiolefin-functional cross-linking agent. A suitable material of this type is described in U.S. Pat. No. 5,570,585—Park et al., the disclosure of which is incorporated herein by reference.

Another suitable material for the micropellets 12 is a porous hydrated polyvinyl alcohol (PVA) foam gel prepared from a polyvinyl alcohol solution in a mixed solvent consisting of water and a water-miscible organic solvent, as described, for example, in U.S. Pat. No. 4,663,358—Hyon et al., the disclosure of which is incorporated herein by reference. Other suitable PVA structures are described in U.S. Pat. No. 5,823,198—Jones et al. and U.S. Pat. No. 5,258,042—Mehta, the disclosures of which are incorporated herein by reference. Another suitable material is a collagen foam, of the type described in U.S. Pat. No. 5,456,693—Conston et al., the disclosure of which is incorporated herein by reference. Still another suitable material is PHEMA, as discussed in the references cited above. See, e.g., Horák et al., supra, and Rao et al., supra.

The preferred foam material, as described in the above-referenced patent to Park et al., has a void ratio of at least about 90%, and its hydrophilic properties are such that it has a water content of at least about 90% when fully hydrated. In the preferred embodiment, each of the embolizing micropellets 12 has an initial diameter of not more than about 0.5 mm prior to expansion in situ, with an expanded diameter of at least about 3 mm. To achieve such a small size, the micropellets 12 may be compressed to the desired size from a significantly larger initial configuration. The compression is performed by squeezing or crimping the micropellets 12 in a suitable implement or fixture, and then "setting" them in the compressed configuration by heating and/or drying. Each of the micropellets 12 is swellable or expansible to many times (at least about 25 times, preferably about 70 times, and up to about 100 times) its initial (compressed) volume, primarily by the hydrophilic absorption of water molecules from an aqueous solution (e.g., resident blood plasma and/or injected saline solution), and secondarily by the filling of its pores with blood. Also, the micropellets 12 may be coated with a water-soluble coating (not shown), such as a starch or a suitable polymer, to provide a time-delayed expansion. Another alternative is to coat the micropellets 12 with a temperature-sensitive coating that disintegrates in response to normal human body temperature. See, e.g., U.S. Pat. No. 5,120,349—Stewart et al. and U.S. Pat. No. 5,129,180—Stewart.

The foam material of the embolizing micropellet 12 may advantageously be modified, or provided with additives, to make the device 10 visible by conventional imaging techniques. For example, the foam can be impregnated with a water-insoluble radiopaque material such as barium sulfate, as described by Thanoo et al., "Radiopaque Hydrogel Microspheres", *J. Microencapsulation*, Vol. 6, No. 2, pp. 233–244 (1989). Alternatively, the hydrogel monomers can be copolymerized with radiopaque materials, as described in Horák et al., "New Radiopaque PolyHEMA-Based Hydrogel Particles", *J. Biomedical Materials Research*, Vol. 34, pp. 183–188 (1997).

The micropellets 12 may optionally include bioactive or therapeutic agents to promote thrombosis, cellular ingrowth, and/or epithelialization. See, e.g, Vacanti et al., "Tissue Engineering: The Design and Fabrication of Living Replacement Devices for Surgical Reconstruction and Transplantation," *The Lancet* (Vol. 354, Supplement 1), pp. 32–34 (July, 1999); Langer, "Tissue Engineering: A New Field and Its Challenges," *Pharmaceutical Research*, Vol. 14., No. 7, pp. 840–841 (July, 1997); Persidis, "Tissue Engineering," *Nature Biotechnology*, Vol. 17, pp. 508–510 (May, 1999).

The filamentous carrier 14 is preferably a length of nickel/titanium wire, such as that marketed under the trade name "Nitinol". Wire of this alloy is highly flexible, and it has an excellent "elastic memory", whereby it can be formed into a desired shape to which it will return when it is deformed. In a preferred embodiment of the invention, the wire that forms the carrier 14 has a diameter of approximately 0.04 mm, and it is heat-treated to form a multi-looped structure that may assume a variety of three-dimensional shapes, such as a helix, a sphere, or an ovoid when unconstrained (as disclosed, for example, in U.S. Pat. No. 5,766,219—Horton, the disclosure of which is incorporated herein by reference). Preferably, the intermediate portion of the carrier 14 (i.e., the portion that includes the micropellets 12) and the proximal portion (that carries the proximal microcoil segment 22) are formed into loops having a diameter of approximately 6 mm, while the distal portion (that carries the distal microcoil segment 18) may have a somewhat greater diameter (e.g., approximately 8–10 mm). The carrier 14 may be formed of a single wire, or it may be formed of a cable or braided structure of several ultra-thin wires.

In another embodiment, the carrier 14 may be made of a thin filament of a suitable polymer, such as a PVA, that is formed in a looped structure. The polymer may be impregnated with a radiopaque material (e.g., barium sulfate or particles of gold, tantalum, or platinum), or it may enclose a core of nickel/titanium wire. Alternatively, the carrier 14 may be constructed as a "cable" of thin polymer fibers that includes fibers of an expansile polymer, such as polyvinyl alcohol (PVA), at spaced intervals to form the micropellets 12.

Still another alternative construction for the carrier 14 is a continuous length of microcoil. In such an embodiment, the micropellets 12 would be attached at spaced intervals along the length of the carrier 14.

Figure 8:
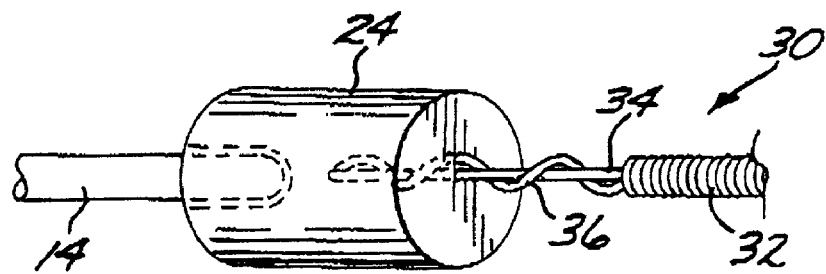
FIG. 8 is a detailed perspective view of mechanism by which the embolization device of the present invention is preferably attached to the distal end of a deployment instrument.
Figure 9:
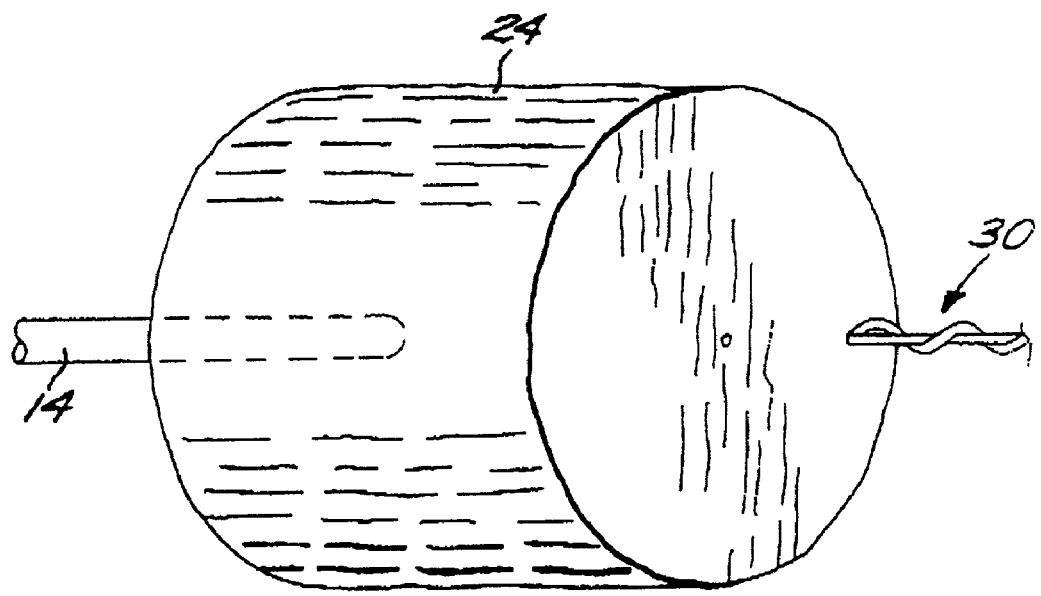
FIG. 9 is a detailed perspective view, similar to that of FIG. 8, showing the embolization device of the present invention after it has been separated from the deployment instrument.

As shown in FIGS. 1, 8, and 9, the hydrogel linkage element 24 is advantageously made of the same material as the micropellets 12. Indeed, the most proximal of the micropellets 12 may function as the linkage element 24. The linkage element 24 is attached to the proximal end of the carrier 14 by a suitable biocompatible adhesive. The purpose of the linkage element 24 is to removably attach the device 10 to a deployment instrument 30 (FIGS. 8 and 9). The deployment instrument 30 comprises a length of platinum or platinum/tungsten microcoil outer portion 32 with a flexible wire core 34 of the same or a similar metal. The deployment instrument 30 has a distal portion 36 at which the microcoil outer portion 32 has coils that are more distantly-spaced (i.e., have a greater pitch).

As shown in FIG. 8, the device 10 is initially attached to the deployment instrument 30 by means of the linkage element 24. Specifically, the linkage element 24 is installed, in a compressed state, so that it encompasses and engages both the proximal end of the embolization device 10 and the distal portion 36 of the deployment instrument 30. Thus, in the compressed state, the linkage element 24 binds the deployment instrument 30 and the embolization device 10 together. As shown in FIG. 9, and as will be described in detail below, after the device 10 is deployed in a vascular site, the linkage element 24 expands greatly, thereby loosening its grip on the distal portion 36 of the deployment instrument 30, and thus allowing the embolization device 10 to be separated from the deployment instrument 30 by pulling the latter proximally out of and away from the linkage element 24.

The Embolization Device: Second Preferred Embodiment. FIGS. 14 through 23 illustrate an embolization device in accordance with a second preferred embodiment of the present invention. Referring first to FIGS. 14 through 17, a device 100 in accordance with this second embodiment comprises an elongate, flexible, filamentous carrier 102 on which an expansile embolizing element 104 is non-releasably carried. The carrier 102 is preferably formed from a continuous length of hollow microcoil 106, made from a suitable metal such as platinum, gold, tungsten, or tantalum, or a metallic alloy, such as stainless steel or Nitinol. Of these materials, platinum and Nitinol are preferred. The microcoil is formed with tightly-packed coils, so that there is little or no spacing between adjacent coils. The carrier 102 may also include a filamentous core 108 extending axially through the microcoil 106. The core 108 is a thin metal wire, preferably made of a shape memory metal such as Nitinol. The device 100 includes a distal portion comprising an outer coil 110 coaxially surrounding the microcoil 106, and terminating in a rounded distal tip 112. A hydrogel linkage element (not shown), of the type described above and illustrated in FIGS. 8 and 9, may advantageously be provided at the proximal end of the carrier.

The carrier 102 may, alternatively, be made of any of the materials described above with respect to the carrier of the first preferred embodiment. While it is preferably in the configuration of a microcoil, it may also be formed as a single strand of metal wire or polymeric filament, or as a multi-strand braid or cable of metal wire or polymeric filament. The carrier should have a column strength sufficient to allow it to be pushed through a microcatheter, as mentioned above.

The expansile embolizing element 104 is advantageously formed as a hydrogel layer covering a substantial portion of the length of the carrier 102. The embolizing element 104 may be made of any of the materials used in the embolizing elements of the above-described first preferred embodiment. Advantageously, however, the embolizing element 104 of this second embodiment is preferably formed of a porous, environmentally-sensitive, expansile hydrogel, of the type described in prior co-pending U.S. patent application Ser. No. 09/804,935 (the disclosure of which is incorporated herein by reference). For the convenience of the reader, a brief description of a suitable formulation of a preferential hydrogel is set forth below.

Specifically, the hydrogels described in the above-referenced prior application are of a type that experience an increase in lubricity and undergo controlled volumetric expansion in an aqueous environment at a rate that changes in response to changes in a physical parameter of the environment, such as its pH or temperature. These hydrogels are prepared by forming a liquid mixture that contains (a) at least one monomer and/or polymer, at least a portion of which is sensitive to changes in an environmental parameter; (b) a cross-linking agent; and (c) a polymerization initiator. If desired, a porosigen (e.g., NaCl, ice crystals, or sucrose) may be added to the mixture, and then removed from the resultant solid hydrogel to provide a hydrogel with sufficient porosity to permit cellular ingrowth. The controlled rate of expansion is provided through the incorporation of ethylenically unsaturated monomers with ionizable functional groups (e.g., amines, carboxylic acids). For example, if acrylic acid is incorporated into the crosslinked network, the hydrogel is incubated in a low pH solution to protonate the carboxylic acids. After the excess low pH solution is rinsed away and the hydrogel dried, the hydrogel can be introduced through a microcatheter filled with saline at physiological pH or with blood. The hydrogel cannot expand until the carboxylic acid groups deprotonate. Conversely, if an amine-containing monomer is incorporated into the crosslinked network, the hydrogel is incubated in a high pH solution to deprotonate amines. After the excess high pH solution is rinsed away and the hydrogel dried, the hydrogel can be introduced through a microcatheter filled with saline at physiological pH or with blood. The hydrogel cannot expand until the amine groups protonate.

More specifically, in a preferred formulation of the hydrogel, the monomer solution is comprised of ethylenically unsaturated monomers, an ethylenically unsaturated crosslinking agent, a porosigen, and a solvent. At least a portion, preferably 10%–50%, and more preferably 10%–30%, of the monomers selected must be pH sensitive. The preferred pH sensitive monomer is acrylic acid. Methacrylic acid and derivatives of both acids will also impart pH sensitivity. Since the mechanical properties of hydrogels prepared exclusively with these acids are poor, a monomer to provide additional mechanical properties should be selected. A preferred monomer for providing mechanical properties is acrylamide, which may be used in combination with one or more of the above-mentioned pH sensitive monomers to impart additional compressive strength or other mechanical properties. Preferred concentrations of the monomers in the solvent range from 20% w/w to 30% w/w.

The crosslinking agent can be any multifunctional ethylenically unsaturated compound, preferably N,N'-methylenebisacrylamide. If biodegradation of the hydrogel material is desired, a biodegradable crosslinking agent should be selected. The concentrations of the crosslinking agent in the solvent should be less than about 1% w/w, and preferably less than about 0.1% w/w.

The porosity of the hydrogel material is provided by a supersaturated suspension of a porosigen in the monomer solution. A porosigen that is not soluble in the monomer solution, but is soluble in the washing solution can also be used. Sodium chloride is the preferred porosigen, but potassium chloride, ice, sucrose, and sodium bicarbonate can also be used. It is preferred to control the particle size of the porosigen to less than about 25 microns, more preferably less than about 10 microns. The small particle size aids in the suspension of the porosigen in the solvent. Preferred concentrations of the porosigen range from about 5% w/w to about 50% w/w, more preferably about 10% w/w to about 20% w/w, in the monomer solution. Alternatively, the porosigen can be omitted and a non-porous hydrogel can be fabricated.

The solvent, if necessary, is selected based on the solubilities of the monomers, crosslinking agent, and porosigen. If a liquid monomer (e.g. 2-hydroxyethyl methacrylate) is used, a solvent is not necessary. A preferred solvent is water, but ethyl alcohol can also be used. Preferred concentrations of the solvent range from about 20% w/w to about 80% w/w, more preferably about 50% w/w to about 80% w/w.

The crosslink density substantially affects the mechanical properties of these hydrogel materials. The crosslink density (and hence the mechanical properties) can best be manipulated through changes in the monomer concentration, crosslinking agent concentration, and solvent concentration. The crosslinking of the monomer can be achieved through reduction-oxidation, -radiation, and heat. Radiation crosslinking of the monomer solution can be achieved with ultraviolet light and visible light with suitable initiators or ionizing radiation (e.g. electron beam or gamma ray) without initiators. A preferred type of crosslinking initiator is one that acts via reduction-oxidation. Specific examples of such red/ox initiators that may be used in this embodiment of the invention are ammonium persulfate and N,N,N',N'-tetramethylethylenediamine.

After the polymerization is complete, the hydrogen is washed with water, alcohol or other suitable washing solution(s) to remove the porosigen(s), any unreacted, residual monomer(s) and any unincorporated oligomers. Preferably this is accomplished by initially washing the hydrogel in distilled water.

As discussed above, the control of the expansion rate of the hydrogel is achieved through the protonation/deprotonation of ionizable functional groups present on the hydrogel network. Once the hydrogel has been prepared and the excess monomer and porosigen have been washed away, the steps to control the rate of expansion can be performed.

In embodiments where pH sensitive monomers with carboxylic acid groups have been incorporated into the hydrogel network, the hydrogel is incubated in a low pH solution. The free protons in the solution protonate the carboxylic acid groups on the hydrogel network. The duration and temperature of the incubation and the pH of the solution influence the amount of control on the expansion rate. Generally, the duration and temperature of the incubation are directly proportional to the amount of expansion control, while the solution pH is inversely proportional. It has been determined that the water content of the treating solution also affects the expansion control. In this regard, the hydrogel is able to expand more in the treating solution and it is presumed that an increased number of carboxylic acid groups are available for protonation. An optimization of water content and pH is required for maximum control on the expansion rate. After the incubation is concluded, the excess treating solution is washed away and the hydrogel material is dried. The hydrogel treated with the low pH solution has been observed to dry down to a smaller dimension than the untreated hydrogel. This is a desired effect, since delivery of these hydrogel materials through a microcatheter is desired, as discussed below.

If pH sensitive monomers with amine groups were incorporated into the hydrogel network, the hydrogel is incubated in high pH solution. Deprotonation occurs on the amine groups of the hydrogel network at high pH. The duration and temperature of the incubation, and the pH of the solution, influence the amount of control on the expansion rate. Generally, the duration, temperature, and solution pH of the incubation are directly proportional to the amount of expansion control. After the incubation is concluded, the excess treating solution is washed away and the hydrogel material is dried.

In yet other embodiments of the embolization device incorporating embolizing elements comprising hydrogel, the formulation of the hydrogel polymer of the member can be modified to incorporate polymers that degrade, or break down, in the body after a period of time in response to, e.g., hydrolysis or enzymatic action, into simpler molecular constituents that can be absorbed by the patient's body and/or eliminated from it as waste. Polymers suitable for incorporation into the embolization device for this purpose include those described in: "Types of Biodegradable Hydrogels," *Biodegradable Hydrogels for Drug Delivery*, K. Park et al., Technomic Publishing 1993, pp. 35–66; U.S. Pat. No. 6,316, 522—Loomis et al.; U.S. Pat. No. 6,224,892—Searle; U.S. Pat. No. 6,201,065—Pathan et al. The disclosures of the foregoing references are incorporated herein by this reference. Thus, in other possible embodiments of the embolization device incorporating an expansile polymer embolizing member, the member can be made such that it is biodegradable and/or bioresorbable in the patient's body, where such properties are clinically indicated.

Figure 14:
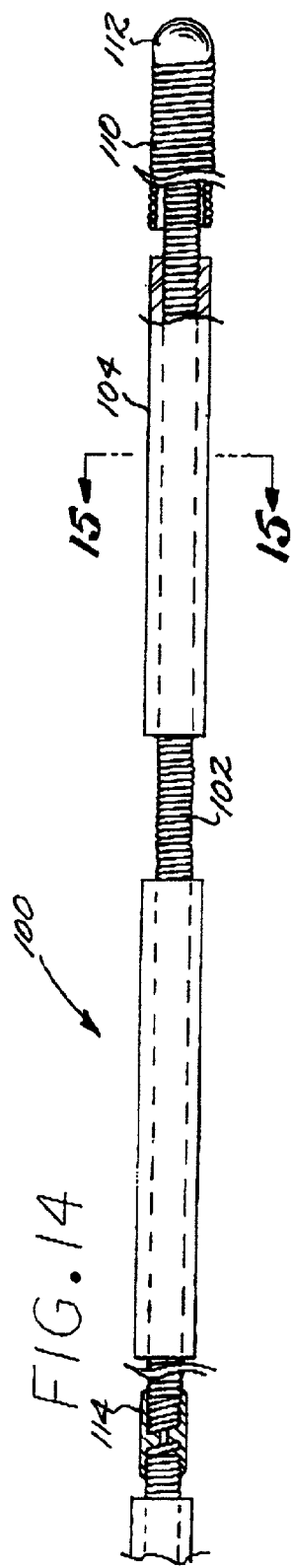
FIG. 14 is an elevational view, partially in section, of an embolic device in accordance with a second preferred embodiment of the invention, showing the device in its normal or non-expanded state.

As shown in FIG. 14, an embolic device 100 in accordance with this second embodiment may include more than one elongate expansile embolizing elements 104. Also, if desired for a particular application, two or more embolizing devices 100 can be joined end-to-end at a juncture 114 formed by a weld or a solder joint.

Figure 16:
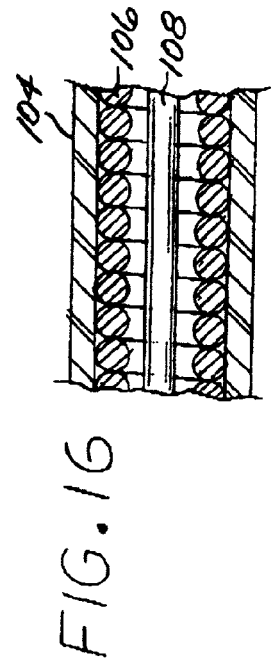
FIG. 16 is a detailed axial cross-sectional view of a portion of the device shown in FIG. 14.
Figure 15:
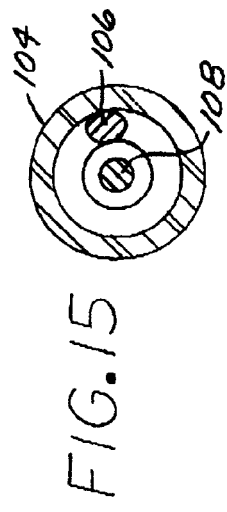
FIG. 15 is a cross-sectional view taken along line 15—15 of FIG. 14.
Figure 17:
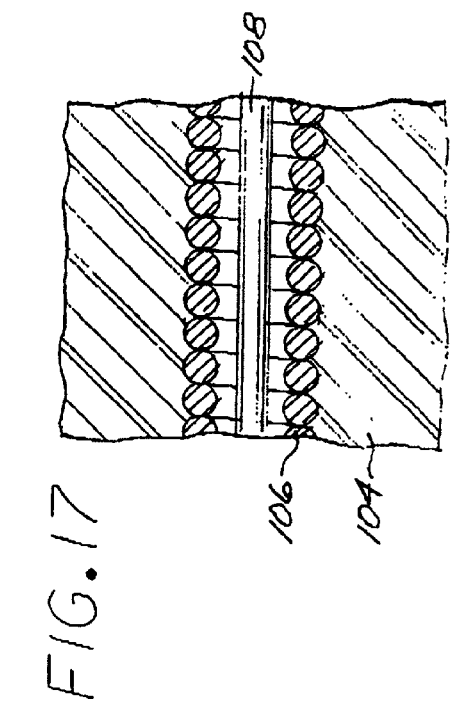
FIG. 17 is a view similar to that of FIG. 16, showing the device of FIG. 14 in its expanded state after deployment in a vascular site.
Figure 18:
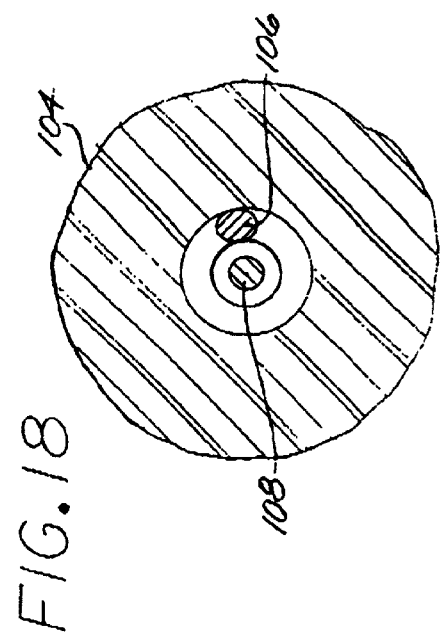
FIG. 18 is a view similar to that of FIG. 15, showing the device of FIG. 14 in its expanded state after deployment in a vascular site.

FIGS. 14, 15, and 16 show the device 100 with the embolizing elements 104 in their non-expanded state. Each embolizing element 104 assumes a tubular configuration in the form of a coating or layer on the exterior surface of the carrier 102. FIGS. 17 and 18 show an embolizing element 104 in its expanded state after deployment in a vascular site. If made from the environmentally-sensitive hydrogel described above, the expansion is a reaction to the pH and/or temperature experienced in the vascular site. The expansion begins between about 1 minute and about 30 minutes after deployment, and preferably about 15 minutes after deployment. This delayed expansion allows the physician sufficient time to reposition and even withdraw the device without the need for a restraining agent, encapsulating layer, or a non-aqueous carrier fluid. When fully expanded, the embolizing element 104 has an expanded volume that is between about two times and about 100 times its non-expanded volume, and preferably between about 3 times and about 25 times its non-expanded volume.

A first modification of this second preferred embodiment is shown in FIGS. 19 and 20. As shown, a modified embolic device 100' comprises an elongate, flexible, filamentous carrier. The carrier comprises an elongate, hollow microcoil 106' that is similar to the microcoil 106 shown in FIGS. 14–17, except that it has significant spaces between adjacent coils. Like the device 100 of FIGS. 14–17, the carrier of the device 100' may advantageously include a central axial core 108', formed of a thin, flexible wire. An expansile embolizing element 104', made of any of the above-described hydrogels, is formed on the carrier so that it resides between adjacent coils of the microcoil 106', thereby encapsulating them. FIG. 19 shows the embolizing element 104' in its non-expanded state, while FIG. 20 shows it in its expanded state, after deployment.

Another modification of the second preferred embodiment is shown in FIGS. 21 and 22. An embolic device 100'' in accordance with this version comprises an elongate, filamentous carrier, preferably in the form of a hollow, flexible microcoil 106''. Although the carrier is shown without a wire core, it is understood that a wire core may be included, as described above. In this version, a plurality of expansile embolizing elements 120 are formed as fibers or threads that are attached to the microcoil 106'' at spaced-apart intervals along its length. Each of the expansile embolizing elements 120 is preferably made of an environmentally-sensitive hydrogel, of the type described in the prior co-pending application described above, although the hydrogel described in the U.S. Pat. No. 5,750,585—Park et al., supra, may also be used, as well as any of the other hydrogel materials described above in connection with the first preferred embodiment of the embolic device. FIG. 21, shows the embolizing elements 120 in their non-expanded state, while FIG. 22 shows them in their expanded state after deployment.

Still another modification of the second preferred embodiment is shown in FIG. 23. An embolic device 100''' in accordance with this version comprises an elongate, filamentous carrier, preferably in the form of a hollow, flexible microcoil 106'''. The carrier may include a wire core, although one is not shown in the drawing. This version includes an elongate coaxial embolizing element 104''' that is in the form of a stretch-resistant outer layer applied to the exterior of the microcoil 106''' along a substantial portion of the its length. The stretch-resistant outer layer is preferably formed of an expansile polymer, such as those described above, but it may also be formed of any stretch-resistant, biocompatible polymer, such as, for example, polyurethane, polyester, polytetrafluoroethylene (PTFE), nylon, polymethylmethacrylate (PMMA), and silicone.

The Embolization Device: Third Exemplary Embodiment and First Method for Making It: A third exemplary embodiment of a device 300 for occluding a body cavity is illustrated in FIGS. 32–35, and a first exemplary embodiment of a method for making the third embodiment of the device 300 is illustrated in FIGS. 24–31.

As shown in FIG. 32, the embolization device 300 comprises an elongated, filamentous carrier 302, and an embolizing element comprising a coaxial member 304 of an expansile, hydrophilic polymer, or hydrogel, described in detail above, encapsulating at least a portion of the length of the carrier.

Although the coaxial polymer embolizing member 304 is shown in the figures as having a substantially cylindrical shape, it should be understood that the member, and indeed, the carrier encapsulated within it, can have a wide variety of other cross-sectional shapes, e.g., polygonal, longitudinally grooved, and the like, depending on the particular application at hand.

The carrier 302 may, as in the first and second embodiments of device described above, comprise either an elongated strand of a flexible, biocompatible material, e.g., a platinum wire, or a flexible tube. However, in a variant incorporating a tubular carrier, such as a tubular braid or the flexible, hollow microcoil 302 described above and illustrated in the exemplary embodiment of FIG. 32, the coaxial polymer member 304 is formed on the carrier by the method described below such that the hollow lumen of the carrier is substantially void of the polymer, thereby defining an axial reservoir 306 in the carrier, as shown in FIG. 35. The reservoir 306 in the carrier 302 constitutes a reservoir in which therapeutic agents, in either a liquid or a solid form, can be disposed for delivery to a patient via emplacement of the device 300 in a body cavity of the patient, as described below.

Figure 24:
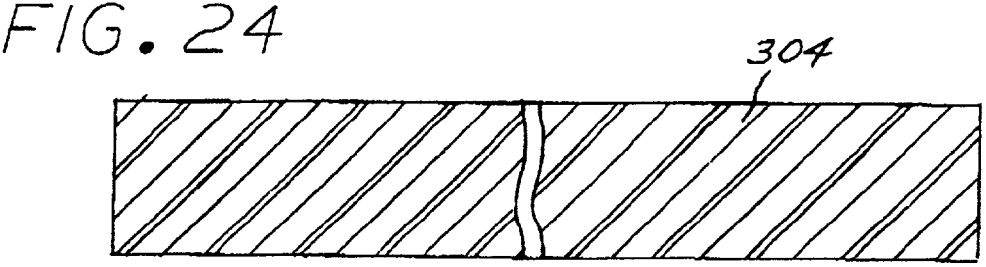
FIG. 24 is a cross-sectional elevation view of a soft, expanded hydrophillic polymer embolizing element in accordance with a first exemplary method for making a third exemplary embodiment of an embolization device in accordance with the invention.

A first exemplary embodiment of a method for making the exemplary third embodiment of the device 300 is illustrated in FIGS. 24–31 of the drawings. With reference to FIG. 24, the method begins with the provision of a softened, elongated member 304 of a expansile, hydrophilic polymer, such as hydrogel. Since the softness of the polymer is a function of the degree of its hydration, the elongated member 304 can be softened by immersing it in a bath of water until it reaches the desired state of softness, viz., about that of fully cooked pasta.

Figure 25:
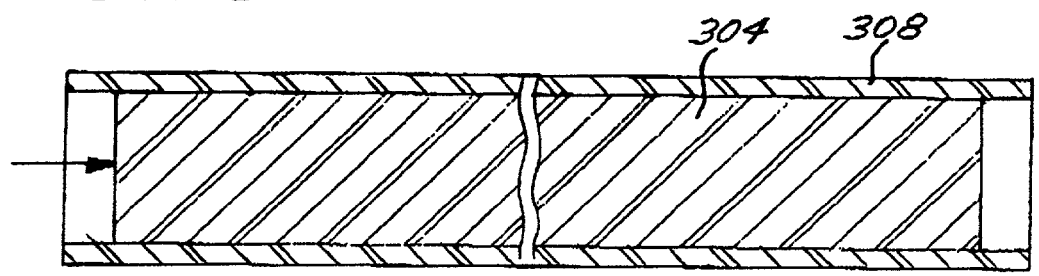
FIG. 25 is a cross-sectional elevation view of the embolizing element of FIG. 24 being inserted into a tubular holder.

When hydrated to the desired state, the softened polymer member 304 is inserted into a tubular holder 308 such that the member is radially confined and axially restrained in the holder, as illustrated in FIG. 25. In one possible embodiment, this is effected by inserting a partially hydrated member 304 into the holder 308, then immersing both in a bath of water until the member expands in the holder to the desired state of support and retention therein.

Figure 26:
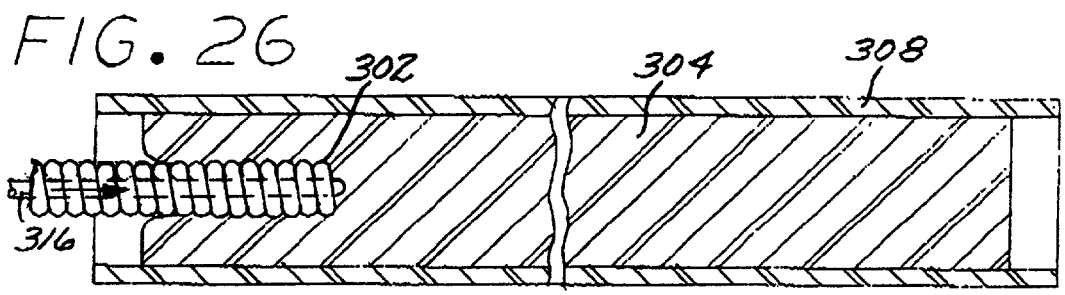
FIG. 26 is a cross-sectional elevation view of the embolizing element of FIG. 25 being coaxially skewered by a helical carrier internally supported by a lumenal mandrel.
Figure 27:
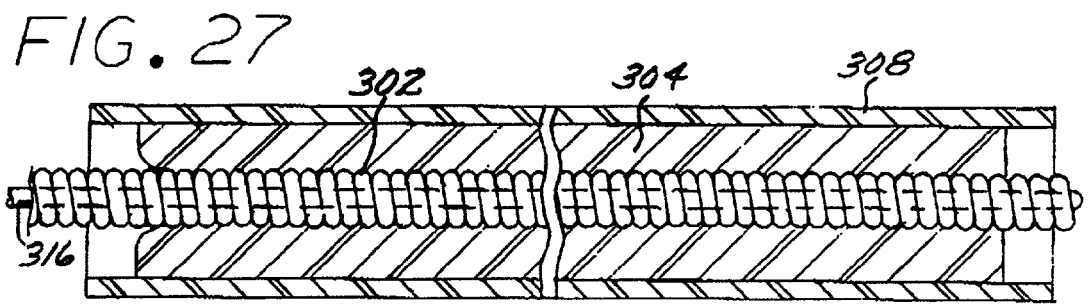
FIG. 27 is a cross-sectional elevation view of the embolizing element of FIG. 26 after being completely skewered by the helical carrier and lumenal mandrel.
Figure 28:
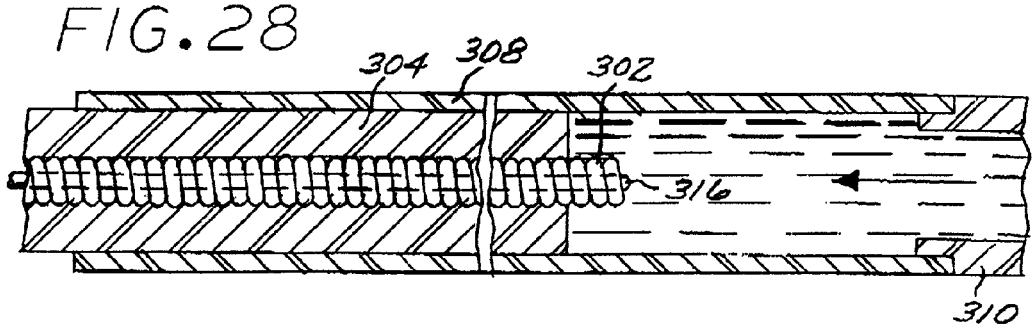
FIG. 28 is a cross-sectional elevation view of the skewered embolizing element of FIG. 27 being ejected from the tubular holder to define an unfinished embolization device in accordance with the third exemplary embodiment thereof.

As illustrated in FIGS. 26 and 27, after the softened polymer member 304 is retained in the holder 308, the member is then coaxially skewered with an elongated, flexible, filamentous carrier 302 such that the polymer member coaxially encapsulates at least a portion of the length of the carrier. In one possible embodiment in which the carrier 302 comprises an elongated strand, such as a wire, this procedure is effected by simply pushing one end of the wire coaxially through the softened member 304, provided the wire is sufficiently straight and stiff, or if not, then by attaching a first end of the wire to the eye of a needle (not illustrated), then forcing the needle through the softened member coaxially, such that the carrier is pulled coaxially through the member by the needle.

In another possible embodiment of the method in which the carrier comprises a flexible tube, such as the helical microcoil 302 illustrated in the figures, a stiff, elongated support mandrel 316 is first inserted coaxially in the lumen of the carrier to straighten and stiffen it, as shown in FIG. 26. The soft polymer member 304 is then coaxially skewered with the carrier supported on the mandrel, such that the polymer member coaxially encapsulates at least a portion of the length of the carrier, as shown in FIG. 27.

After the skewering process, the skewered polymer member 304 and carrier 302 are ejected from the tubular holder 308 to define a partially finished embolization device 300. In the exemplary embodiment illustrated in FIG. 28, this ejection is effected by placing a nozzle 310 against one end of the tubular holder 308 and forcing the skewered member 304 out of the other end of the holder with hydraulic pressure applied through the nozzle.

Figure 29:
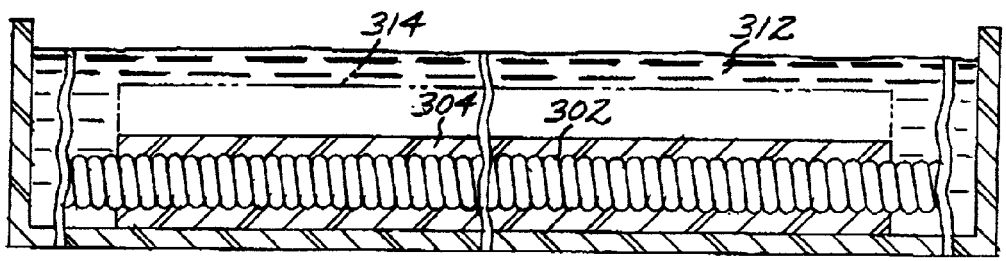
FIG. 29 is a cross-sectional elevation view of the embolization device of FIG. 28 being dehydrated in a bath of a desiccant to shrink the embolizing element thereof.

After the device 300 is removed from the holder 308, the lumenal mandrel 316 may be withdrawn from the device to define the axial reservoir 306 in the carrier 302, as shown in FIG. 35, or alternatively, the mandrel may be left in the carrier to support the device during the subsequent processes applied to it. As shown in FIG. 29, the first of these post-skewering processes comprises dehydrating the coaxial polymer member 304 of the device 300, e.g., by immersion of the device in a hygroscopic medium, e.g., an alcohol bath 312, to remove water from, and thereby shrink, the coaxial polymer member radially from its original soft, expanded size, represented by the phantom outline 314 in FIG. 29, to a thinner, drier member more suitable for passage through the lumen of a catheter, as illustrated.

Figure 30:
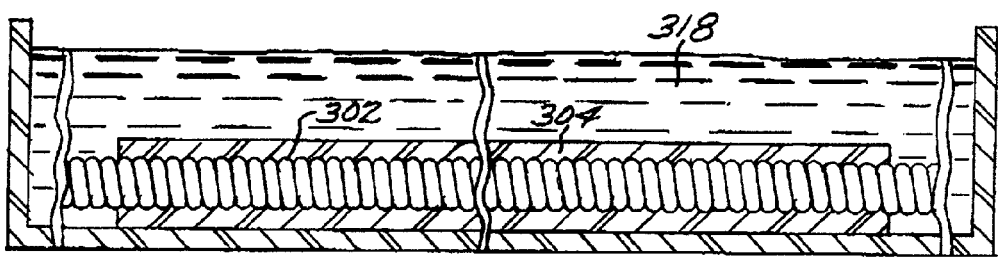
FIG. 30 is a cross-sectional elevation view of the embolization device of FIG. 29 immersed in a bath of an acid to adjust the rate of hydration of the embolizing element in response to a level of a physical parameter of an aqueous environment.
Figure 31:
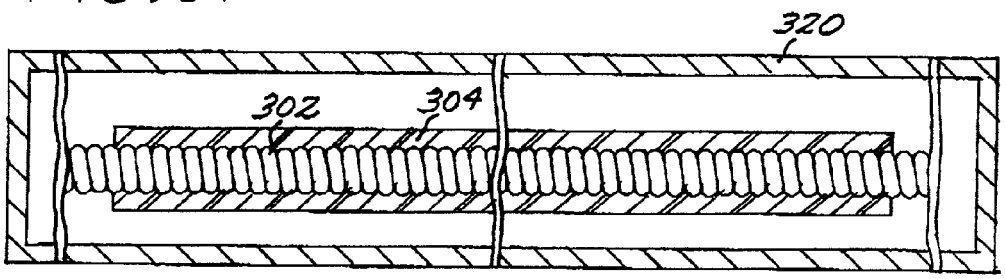
FIG. 31 is a cross-sectional elevation view of the embolization device of FIG. 30 being baked in an oven to dry the embolizing element thereof.

After the dehydration process, the polymer member 304 of the device 300 is washed, then treated, e.g., by immersing the device in an acid bath 318 of a selected strength and for a selected period of time, as illustrated in FIG. 30, to set the rate of hydration of the polymer, and hence, the rate of expansion, of the coaxial polymer member 304, in an aqueous environment, e.g., blood or plasma, in response the level of a physical parameter of that environment, e.g., its temperature or pH level, as described above. After the hydration rate of the device 300 has been set, it is washed, preferably in a solution of water and alcohol, to remove any processing impurities, and then dried by heating, e.g., by baking in an oven 320, as illustrated in FIG. 31. The dry, finished embolization device 300 may then be packaged in a sterile container for storage or shipment.

Figure 37:
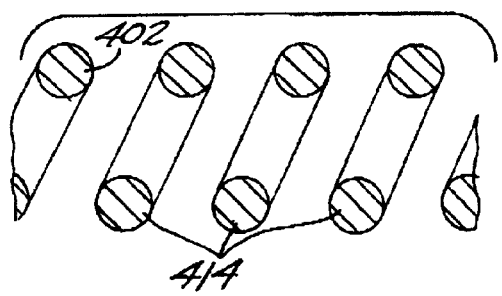
FIG. 37 is an enlarged, partial cross-sectional view into the nascent embolization device of FIG. 36, as revealed by the section taken therein along the lines 37—37, showing a carrier of the device.
Figure 38:
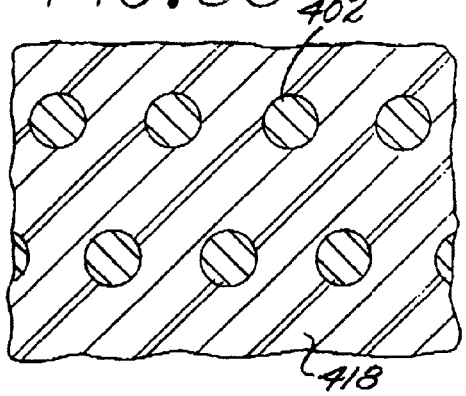
FIG. 38 is an enlarged, partial cross-sectional view similar to that of FIG. 37, showing the carrier being encapsulated in a polymer.

The Embolization Device: Fourth Exemplary Embodiment and Second Method for Making It: A fourth exemplary embodiment of an embolization device 400 for occluding a body cavity is illustrated in FIGS. 39–42, and a second exemplary embodiment of a method for making the fourth embodiment of the device 400 is illustrated in FIGS. 36–38.

Figure 39:
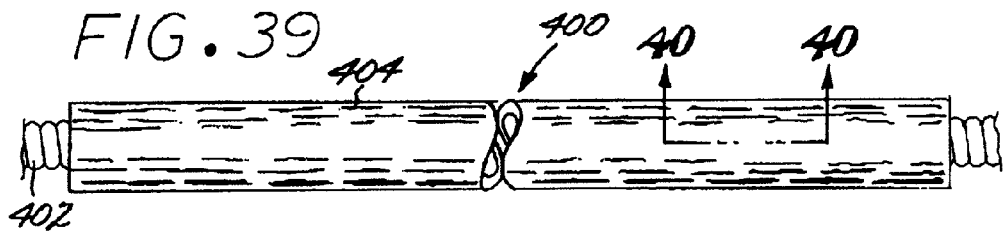
FIG. 39 is an elevational view of one variant of the fourth exemplary embodiment of the embolization device.
Figure 41:
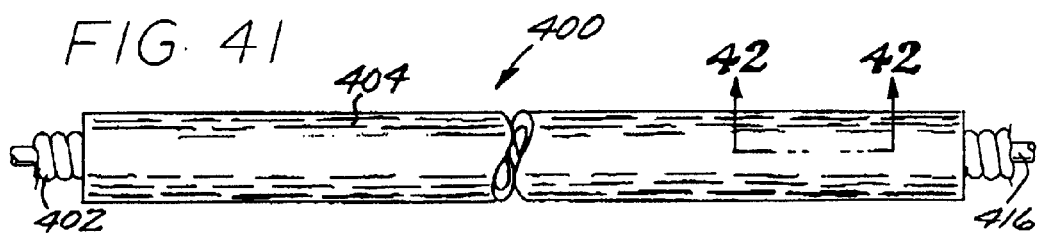
FIG. 41 is an elevational view of another variant of the fourth exemplary embodiment of the embolization device, showing a lumenal mandrel in the carrier of the device.

As illustrated in FIGS. 39 and 41, respectively, two possible variants of the fourth exemplary embodiment of embolization device 400 both comprise, as in the case of the third exemplary embodiment 300 described above, an elongated, filamentous carrier 402, and a coaxial member 404 of an expansile, hydrophilic polymer, or hydrogel, encapsulating at least a portion of the length of the carrier. Further, in both variants, the carrier 402 may, like the third embodiment above, comprise either an elongated strand of a flexible, biocompatible material, e.g., platinum wire, or a flexible tube.

Figure 40A:
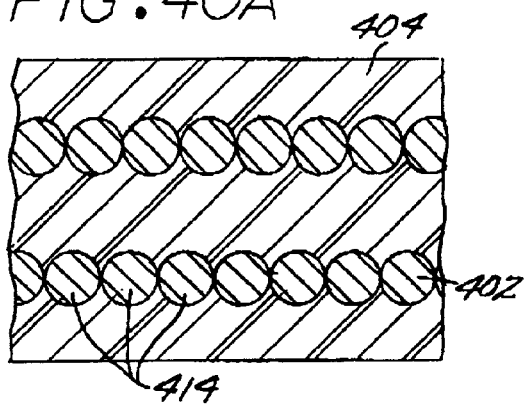
FIG. 40A is an enlarged, partial cross-sectional view into the embolization device of FIG. 39, as revealed by the section taken therein along the lines 40—40, showing one possible variant thereof in which the coils of a helically coiled carrier are spaced close together.
Figure 40B:
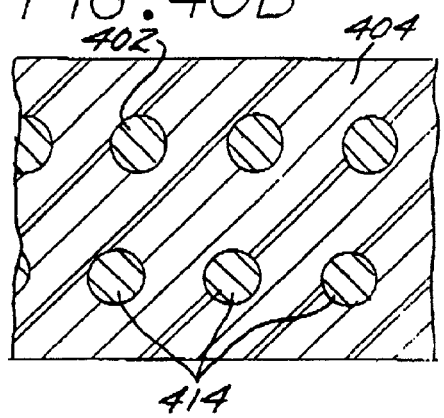
FIG. 40B is a view similar to that of FIG. 40A, showing another variant in which the coils of the carrier are spaced apart from each other.

However, in contrast to the third embodiment of the device 300 above, in the first variant incorporating a tubular carrier, such as the flexible, hollow microcoil 402 described above and illustrated in the exemplary embodiment of FIG. 39, the coaxial polymer member 404 is formed on the carrier by the method described below in such a way that the lumen of the carrier is substantially occupied by the polymer, whereby no axial reservoir is created in the carrier, as illustrated in the enlarged cross-sectional views thereof of FIGS. 40A and 40B.

Alternatively, in the second variant of the device 400 illustrated in FIG. 41, which also incorporates a tubular carrier, viz., a flexible, hollow microcoil 402, the coaxial polymer member 404 can be formed on the carrier in a variation of the method described below such that the hollow lumen of the carrier is substantially void of the polymer, thereby defining an axial reservoir 406 in the carrier, as illustrated in FIGS. 42A and 42B, in a manner similar to that created in the third embodiment 300 described above and illustrated in FIG. 35.

The second exemplary embodiment of a method for making the exemplary fourth embodiment of the device 400 is illustrated in FIGS. 36–38. Referring to FIG. 36, the method begins with the provision of a mold 408 having an elongated cavity 410 therein. The mold 408 may also include a vent 412 for venting air from the cavity 410 during the molding operation described below.

An elongated filamentous carrier 402, which may comprise a tubular, helically coiled carrier, as above, is disposed coaxially within the cavity 410 of the mold 408. In one possible variant of the method in which a tightly-coiled helical carrier 402 is employed, the carrier is elastically stretched along its axis, such that the coils 414 of the carrier are held spaced apart from each other while the carrier is disposed in the mold 408, as shown in the enlarged cross-sectional view of FIG. 37. In another possible variant, the coils 414 of a helical carrier 402 are formed such that they are spaced apart permanently, i.e., without stretching the carrier in the mold 408. In yet another possible variant of the method, a support mandrel 416 is inserted coaxially in the lumen of a helical carrier 402, which may have either closely spaced or spaced-apart helical coils 414, in a manner similar to that described above in connection with the first method, before the carrier is disposed in the cavity 410 of the mold 408.

When the carrier 402 is disposed in the cavity 410 of the mold 408, a quantity of a expansile, hydrophilic polymer 418, which has been softened by hydration to a viscosity that is about the same as that described above in connection with the first exemplary method embodiment, is transferred into the mold under pressure, as illustrated in FIG. 36, such that the polymer is molded by the cavity into a member 404 that coaxially encapsulates at least a portion of the length of the carrier 402, and in those variants in which the carrier comprises a lumen that is not occupied by a mandrel 416, such that the polymer also flows into and substantially occupies the lumen of the carrier, as illustrated in the enlarged cross-sectional view of FIG. 38.

After the polymer member 404 has been molded onto the carrier 402, the partially finished embolization device 400 is released from the mold 408. The appearance of the molded device 400 is similar to those illustrated in FIGS. 39 and 41, except that the molded polymer member 404 is still soft and swollen by hydration. Consequently, in those variants of the method in which a helical carrier 402 has been retained in the mold 408 in an elastically stretched condition, this release from the mold causes the adjacent coils 414 of the carrier to spring back into contact with one another through the still-soft polymer member 404, as shown in the enlarged cross-sectional view of FIG. 40A. In those variants of the method in which a helical carrier 402 has been retained in the mold 408 in a permanently expanded condition, the adjacent coils 414 of the carrier do not spring back elastically, but remain spaced apart in the polymer member 404 after the device is released from the mold, as shown in the enlarged cross-sectional view of FIG. 40B. In either case, however, it may be seen that, in both of these variants of the method, the lumen of the carrier 402 is fully occupied by the polymer 418 of the member 404, such that no axial reservoir is formed in the carrier.

However, in those variants of the method incorporating a support mandrel 416 inserted in the lumen of a tubular carrier 402 before the molding, such as that illustrated in FIG. 41, removal of the mandrel from the molded device 400, which may be effected at any stage after molding and before packaging of the device, results in a lumenal reservoir 406 being defined in the carrier of the device similar to that formed by the first exemplary method described above, as illustrated in the enlarged cross-sectional views of FIG. 42A, in which the coils 414 of the helical carrier are shown having returned to a tightly coiled state, and FIG. 42B, in which the coils of the carrier are shown in a permanently spaced-apart condition.

The post-molding processes applied to the fourth exemplary embodiment of the embolization device 400 are substantially the same as those applied to the third exemplary embodiment of the device 300 in the first exemplary method described above, including dehydration of the coaxial member 404, adjustment of its rate of hydration, and the washing, drying and sterile packaging of the device.

It may be seen from the foregoing description that, in both the first and second exemplary methods, the lumenal support mandrel 316 or 416 can be removed from the carrier 302 or 402 at any stage of the process after the skewered or molded coaxial member 304 or 404 is ejected or released from the holder 308 or mold 408, and before the dried and finished device 300 or 400 is packaged. Removal of the mandrel creates an axial reservoir 306 or 406 in the carrier that, as described above, can be used as a receptacle for the delivery of therapeutic agents, e.g., medications, blood cells, and the like, to a patient via implantation of the device.

A wide variety of therapeutic agents, in either liquid or solid form, can be effectively delivered via the axial cavities 306, 406 of the devices 300, 400, and includes such agents as: drugs; growth factors; proteins; clotting agents; sclerosants; anti-infectives, such as antibiotics and antiviral agents; chemotherapeutic agents; anti-rejection agents; analgesics and analgesic combinations; anti-inflammatory agents; hormones, such as steroids; growth factors; and, other naturally derived or genetically engineered proteins, polysaccharides, glycoproteins, or lipoproteins. Thus, an exemplary method for delivering a therapeutic agent to a patient comprises providing an embolization device 300 or 400 in accordance with the third or fourth exemplary embodiments thereof described above, disposing a therapeutic agent in the axial reservoir 306 or 406 of the carrier 302 or 402 of the device, and implanting the device in a body cavity of the patient in accordance with one of the methods described below.

Moreover, in both the third and fourth exemplary embodiments of the device 300 and 400, it will be seen that the properties of the hydrophilic polymer is such that the flexibility, size, and lubricity of the polymer of the coaxial embolizing member 304, 404, and hence, the device itself, all increase with the degree of hydration of the polymer. Further, in accordance with one exemplary embodiment of this invention, the rate of hydration of the polymer in response to a physical parameter, e.g., the pH or temperature, of an aqueous environment, can be set at the time of device manufacture.

Thus, in one exemplary embodiment of a method for preparing a fully dehydrated device 300 or 400 for insertion into a body cavity via a catheter, as described below, the dry device is first immersed in an aqueous medium, e.g., a saline solution, having a relatively low pH level of about 5, such that the rate of hydration of the coaxial polymer member in the medium is correspondingly relatively slow. This increases both the flexibility and the lubricity of the device 300 or 400 such that it can easily be inserted into and pushed through the lumen of the catheter and into the target body cavity, but at a rate that is slow enough to prevent the device from expanding so much that it cannot then be inserted into or moved easily through the catheter, thereby affording the practitioner ample time, e.g., between about 5 and 15 minutes, in which to implant the device in the patient. However, once the device is emplaced in the cavity, its rate of hydration increases substantially in response to the increased physiological pH level of the surrounding aqueous environment, e.g., blood or plasma, which have pH levels of between about 7.0 and 7.5, such that the coaxial member of the device then rapidly expands to occlude the cavity.

Additionally, as described above, the formulation of the polymer of the coaxial member 304 or 404 can be modified to incorporate polymers that degrade, or break down after a period of time by, e.g., hydrolysis or enzymatic reaction in the body cavity into simpler molecular constituents that can be easily and safely absorbed by the body and/or eliminated from it as waste. Thus, in another possible embodiment of the device incorporating a coaxial embolizing member comprising hydrogel, the member can be made such that it is biodegradable and/or bioresorbable in the patient's body.

FIG. 43 illustrates a quick and convenient method known in the industry for determining the flexibility, or conversely, the stiffness, of an embolization device in accordance with this invention, as taught in, e.g., U.S. Pat. No. 5,690,666—A. Berenstein et al. As shown in FIG. 43, an exemplary device 420 is supported on a first horizontal surface 422 such that a portion 424 of the device overhangs a second horizontal surface 426 disposed vertically below the first surface by an arbitrary, fixed height 428, and such that the unsupported end 430 of the overhanging portion just touches the second surface.

It may be seen that, in this arrangement, the overhanging portion 424 of the device 420 takes on a curved shape, due to the weight of the overhanging portion, as shown in the enlarged, partial cross-sectional detail view of FIG. 44, and the horizontal distance 432 between the unsupported end 430 and the supported end 434 of the overhanging portion provides a measure of the flexibility, or conversely, the stiffness of the device. Thus, the stiffer the device, the longer the horizontal distance 432 between the two ends 430 and 434, and vice-versa.

Measured in accordance with the foregoing method, and for a fixed height 428 of about 0.75 in. (19.1 mm), an exemplary embolization device in accordance with the present invention may have, by way of example and without limitation, a stiffness, or flexibility, as indicated by the horizontal distance 432 between the two ends 430 and 434, of more than about 2.25 inches (57.2 mm) when the hydrogel is in a dry (i.e., least flexible) state, between about 1.5 in. (38.2 mm) and 2.25 in. (57.2 mm) when the hydrogel is in a moderately hydrated (i.e., more flexible) state, and less than about 1.5 in (38.2 mm) when the hydrogel is in a fully hydrated (i.e., most flexible) state.

The Method for Embolizing a Vascular Site. One method of embolizing a vascular site using either the embolization device 10 (first preferred embodiment) or the embolizing device 100 (second preferred embodiment) is illustrated in FIGS. 4 through 7. This method will be described with reference to the embolic device 10 of the first preferred embodiment, but it will be appreciated that this method is equally applicable to the device 100 of the second preferred embodiment.

Figure 4:
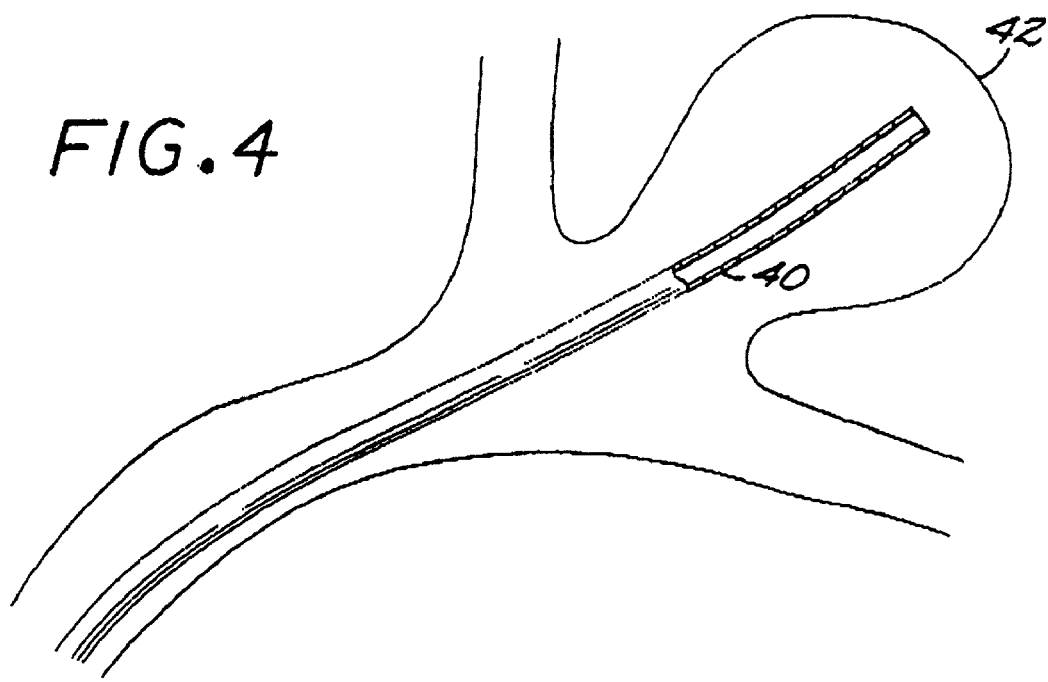
FIGS. 4 through 7 are semischematic views showing the steps in a method of embolizing a vascular site (specifically, an aneurysm) in accordance with one embodiment of the embolizing method aspect of the present invention.
Figure 5:
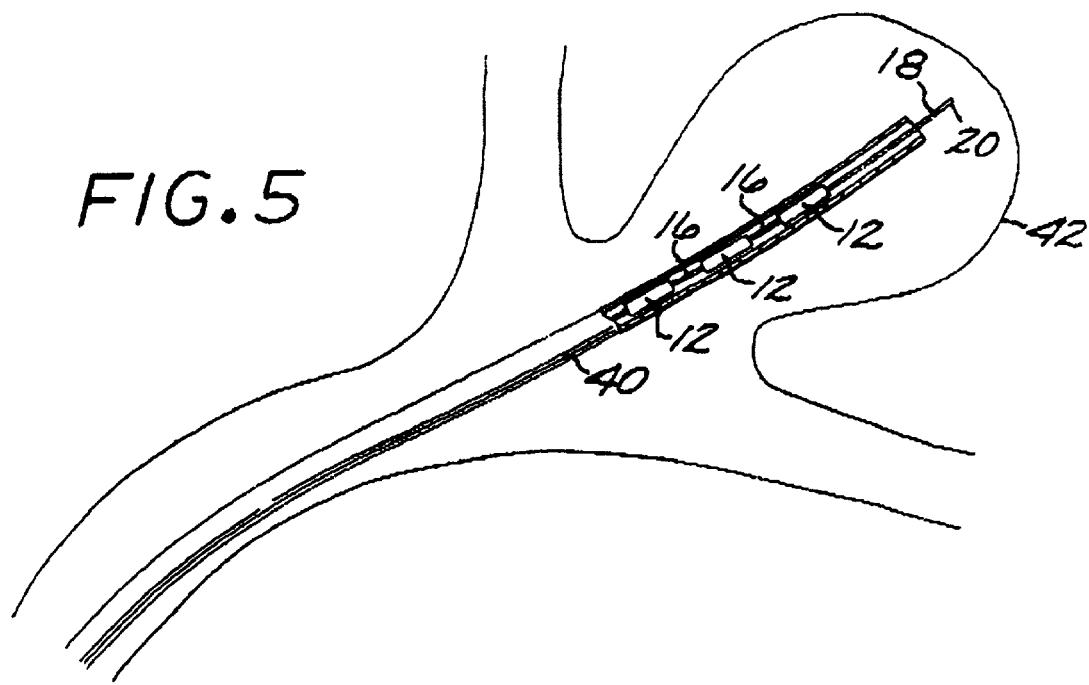
Figure 6:
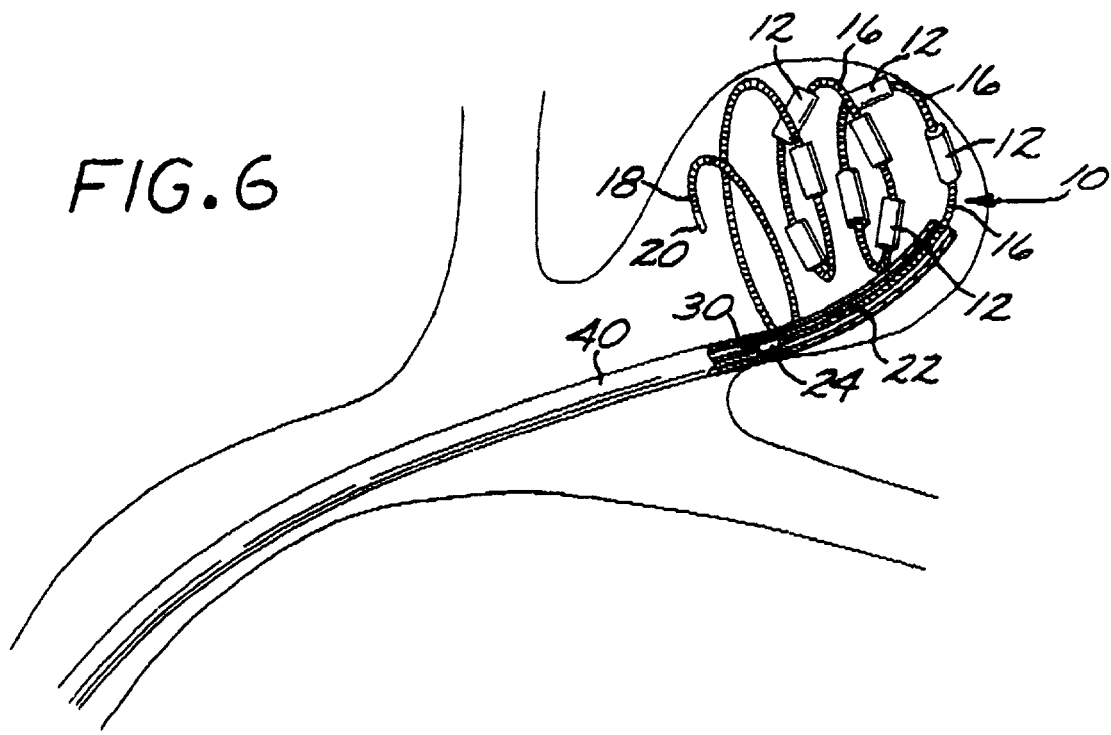

First, as shown in FIG. 4, a microcatheter 40 is threaded intravascularly, by known methods, until its distal end is located within the targeted vascular site (here, an aneurysm 42). Briefly described, this threading operation is typically performed by first introducing a catheter guidewire (not shown) along the desired microcatheter path, and then feeding the microcatheter 40 over the catheter guidewire until the microcatheter 40 is positioned adjacent the distal aspect of the dome of the aneurysm, as shown in FIG. 4. The catheter guidewire is then removed. Then, as shown in FIGS. 5 and 6, the embolization device 10, which is attached to the distal end of the deployment instrument 30, as described above, is passed axially through the microcatheter 40, using the deployment instrument 30 to push the device 10 through the microcatheter 40 until the device 10 is clear from the distal end of the microcatheter 40 and fully deployed within the aneurysm 42 (FIG. 6), filling the aneurysm from its distal aspect. The deployment procedure is facilitated by the visualization of the embolization device 10 that is readily accomplished due to its radiopaque components, as described above.

In the first preferred embodiment, the embolization bodies or micropellets 12, in their compressed configuration, have a maximum outside diameter that is less than the inside diameter of the microcatheter 40, so that the embolization device 10 can be passed through the microcatheter 40. The micropellets 12 are preferably compressed and "set", as described above, before the device 10 is inserted into the microcatheter 40. When inserting the device 10 into the microcatheter 40, a biocompatible, substantially non-aqueous fluid, such as polyethylene glycol, may be injected into the microcatheter 40 to prevent premature expansion of the device 10 due to hydration, and to reduce friction with the interior of the microcatheter 40.

As shown in FIG. 6, when the embolization device 10 is exposed from the microcatheter 40 into the interior of the vascular site 42, the pores of the embolizing bodies or micropellets 12, and of the linkage element 22, begin to absorb aqueous fluid from the blood within the vascular site 42 to release their "set", allowing these elements to begin assuming their expanded configuration. The expansion can be enhanced and accelerated by injecting saline solution through the microcatheter 40. The expansion of the linkage element 24 allows the embolization device 10 to be separated from the deployment instrument 30, as described above, and the deployment instrument 30 can then be removed. Also, the elastic memory of the carrier 14 causes it to resume its original looped configuration once it is released from the confines of the microcatheter 40. Thus, almost immediately upon its release into the vascular site (aneurysm) 42, the embolization device begins to occupy a significant portion of the volume of the aneurysm 42.

Figure 7:
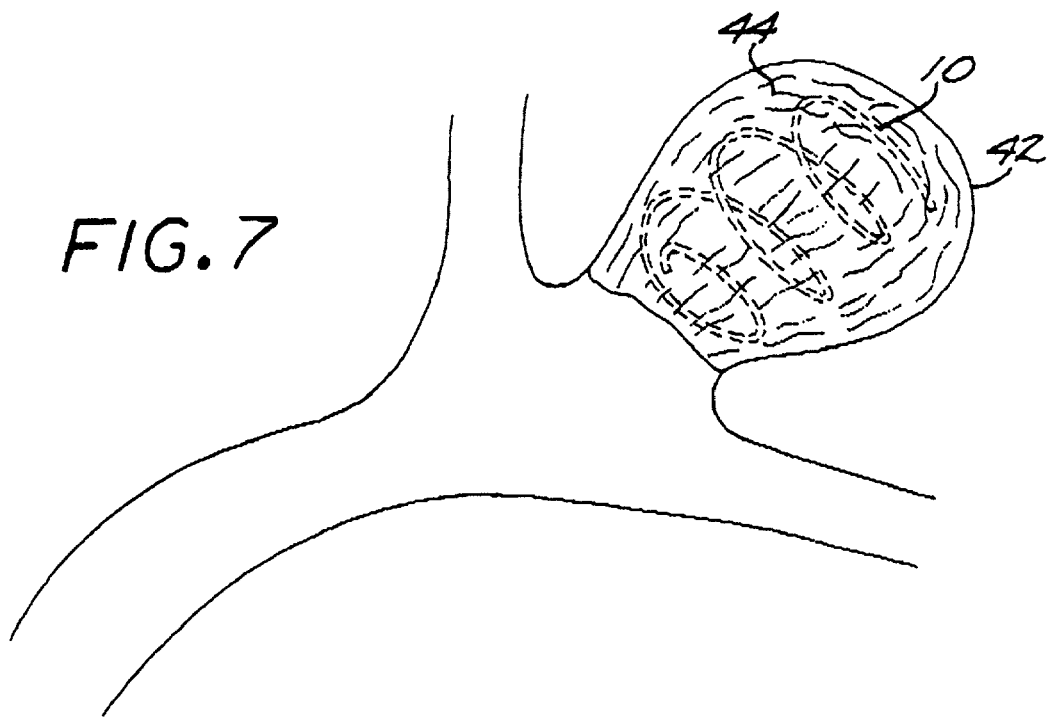

If the micropellets 12 are of a hydrophilic material, they then continue to expand in situ due to hydrophilic hydration of the material, as well as from the filling of their pores with blood. If the embolizing bodies 12 are of a non-hydrophilic material, their expansion is due to the latter mechanism only. In either case, the result, as shown in FIG. 7, is the substantially complete filling of the interior of the aneurysm 42 with the expanded embolizing bodies or micropellets 12, whereby a substantially conformal embolizing implant 44 is formed that substantially fills the interior of the aneurysm 42. The micropellets 12, being non-releasably carried by the carrier 14 and fixed in place thereon, stay on the carrier during their expansion. Thus, the chance of a micropellet separating from the carrier and migrating out of the vascular site is minimized.

In the second preferred embodiment, the embolizing element 104 is not compressed in its initial configuration. Rather, it initially has a configuration in which its outside diameter is small enough to pass through the typical microcatheter. Once deployed within the target vascular site, the embolizing element 104 expands solely by hydration.

It may be advantageous, prior to performing the procedural steps described above, preliminarily to visualize the aneurysm 42, by conventional means, to obtain a measurement (or at least an approximation) of its volume. Then, a device 10 of the appropriate size can be selected that would expand to fill the measured or estimated volume.

Figure 10:
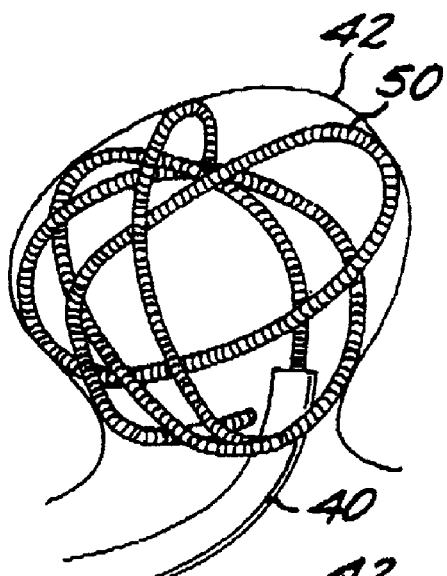
FIGS. 10, 11, and 12 are semischematic views showing steps that, in addition to those illustrated in FIGS. 4–7, constitute a method of embolizing a vascular site in accordance with a preferred embodiment of the embolizing method aspect of the present invention.
Figure 11:
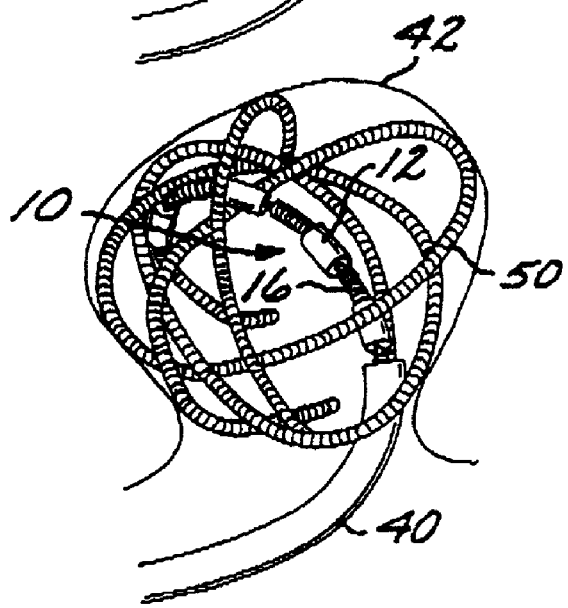
Figure 12:
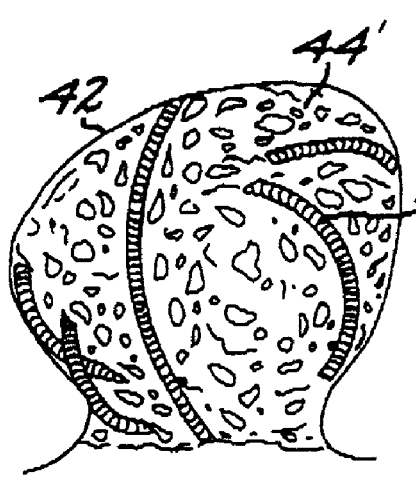

A preferred method of embolizing a target vascular site using the embolization device 10 will be understood with reference to FIGS. 10–12, along with FIGS. 4–7 (discussed above). In this preferred embodiment of the method, the passing of a microcatheter 40 intravascularly until its distal end is introduced into a target vascular site (FIG. 4) is followed by the step of passing a vaso-occlusive device 50 through the microcatheter 40 into the target vascular site (e.g., the aneurysm 42) so that the vaso-occlusive device 50 assumes a three-dimensional configuration that fills a portion of the interior volume of the target vascular site 42, as shown in FIG. 10. The deployed vaso-occlusive device 50 forms a "cage" within the aneurysm 42 that provides a matrix for improved retention of the expansible embolizing bodies or micropellets 12 of the embolization device 10. The embolization device 10 is then passed through the microcatheter 40, as described above, and as shown in FIG. 11, to enter the aneurysm 42 within the voids left by the vaso-occlusive device 50. Finally, the embolizing bodies or micropellets 12 are expanded, as described above, and as shown in FIG. 12, whereby a substantially conformal embolizing implant 44' is formed that fills a substantial portion of the interior volume of the aneurysm 42. Specifically, at least about 30%, and preferably at least about 40% of the interior volume is filled, and, it is believed that in some situations, as much as about 80% to 90% of the interior volume may be filled.

Preferably, the vaso-occlusive device 50 is of the type that is initially in the form of an elongate, flexible, filamentous element for delivery through the microcatheter, and that assumes a three-dimensional geometry (either by elastic behavior or by shape memory) upon installation in the target vascular site. Such devices are describe in, for example, U.S. Pat. Nos. 5,122,136—Guglielmi et al.; U.S. Pat. No. 5,766, 219—Horton; U.S. Pat. No. 5,690,671—McGurk et al.; and U.S. Pat. No. 5,911,731—Pham et al., the disclosures of which are incorporated herein by reference. Still other types of vaso-occlusive devices known in the art may also perform satisfactorily in this method. For example, a stent-like device like that shown in U.S. Pat. No. 5,980,554—Lenker et al. may be employed Alternatively, the vaso-occlusive device 50 may be designed or installed only to enter the space near the opening or "neck" of the aneurysm. In any case, the purpose of the vaso-occlusive device 50 in this method is to present a structural framework that helps retain the embolization device 10 in place within the target vascular site.

Figure 13:
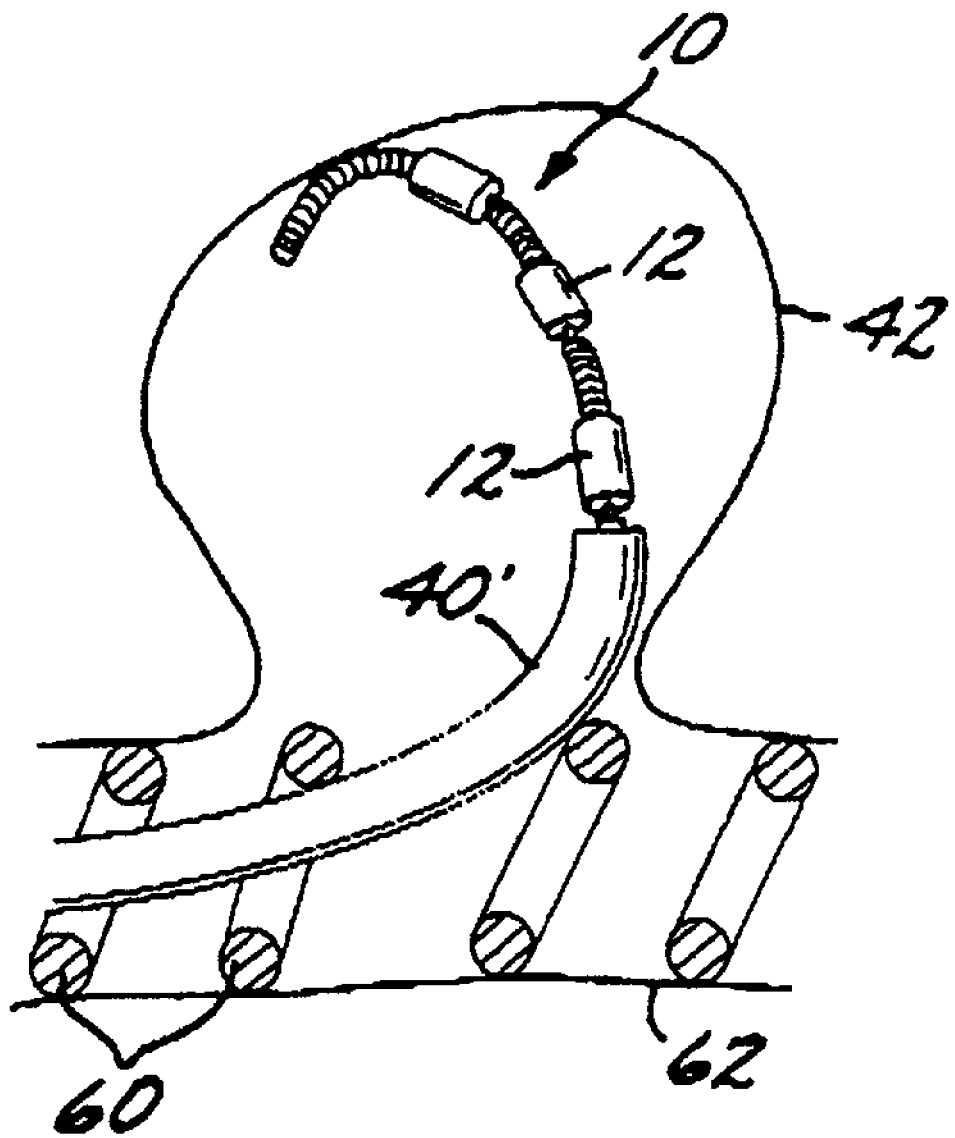
FIG. 13 is a semischematic view showing a step in a method of embolizing a vascular site in accordance with an alternative embodiment of the embolizing method aspect of the present invention.

An alternative embodiment of the method of the present invention will be understood with reference to FIG. 13. In this alternative embodiment, the method includes the preliminary step of deploying an intravascular device 60 to a position in a blood vessel 62 adjacent to a target vascular site 42. A microcatheter 40' is passed intravascularly so that its distal end passes through the intravascular device 60 into the target vascular site 42. The embolization device 10 is passed through the microcatheter 40' so that it emerges from the distal end of the microcatheter 40' into the target vascular site 42, and the embolizing elements 12 are then expanded in situ, as described above, substantially to fill the volume of the target vascular site 42 (as shown in FIGS. 7 and 12).

It is understood that the step of deploying an intravascular device to a position in a blood vessel adjacent to a target vascular site would include any sub-steps necessary for such deployment. For example, if the intravascular device 60 is of the type disclosed in U.S. Pat. No. 5,980,514—Kupiecki et al. (the disclosure of which is incorporated herein by reference), the deployment step would comprise the sub-steps of (i) passing of a microcatheter intravascularly so that its distal end is located adjacent the target vascular site; (ii) passing the intravascular device through the microcatheter until it emerges from the distal end of the microcatheter; and (iii) allowing the intravascular device to assume a three-dimensional configuration adjacent to the target vascular site. In this case, either the microcatheter used for deploying the intravascular device could be removed and then another microcatheter used to install the embolization device, or the intravascular deployment microcatheter could be repositioned for the introduction of the embolization device.

In this alternative method, the intravascular device presents an obstruction that at least partially blocks the juncture between the target vascular site and the blood vessel (e.g., the neck of an aneurysm). Thus, the intravascular device helps retain the embolization device in its proper position within the target vascular site.

It will be apparent that the method of using the second preferred embodiment of the device will be substantially similar to the above-described method.

Although the embolic device in accordance with the present invention has been described above for use in embolizing aneurysms, other applications will readily suggest themselves. For example, it can be used to treat a wide range of vascular anomalies, such as arteriovenous malformations and arteriovenous fistulas. Certain tumors may also be treated by the embolization of vascular spaces or other soft tissue voids using the present invention. The devices may also be used to occlude fallopian tubes for the purposes of sterilization, and the occlusive repair of cardiac defects, such as a patent foramen ovale, patent ductus arteriosis, and left-atrial-appendage and atrial-septal defects. In such circumstances, the occlusion device functions to substantially block the flow of body fluids into or through the cavity, lumen, vessel, space or defect for the therapeutic benefit of the patient.

While preferred embodiments of the invention have been described above, a number of variations and modifications may suggest themselves to those skilled in the pertinent arts. For example, the initial shape and number of embolizing bodies or elements may be varied, as well as the length of the carrier. Furthermore, other mechanisms may be found for removably attaching the embolization device to the deployment wire. One such alternative attachment mechanism may be a transition polymer joint that loosens when heated by contact with blood or by a low-level electric current. These and other variations and modifications are considered within the spirit and scope of the invention, as described in the claims that follow.

What is claimed is:

1. A device for embolizing a body cavity, the device comprising:

an elongated, flexible, filamentous carrier having a looped portion; and a member of an expansile, hydrophilic polymer coaxially encapsulating at least a portion of the looped portion of the carrier.

2. The device of claim 1, wherein the carrier includes an axial lumen, and wherein the polymer of the member substantially fills the lumen of the encapsulated portion of the carrier.

3. The device of claim 1, wherein the carrier includes an axial lumen having an axial reservoir therein.

4. The device of claim 1, wherein the carrier comprises a filamentous element selected from the group consisting of a flexible wire, helical coil, and tube.

5. The device of claim 1, wherein the coaxial member is cylindrical.

6. The device of claim 1, wherein the coaxial member comprises hydrogel.

7. The device of claim 1, wherein the coaxial member is at least one of biodegradable and bioresorbable.

8. The device of claim 1, wherein the coaxial member has a substantially greater lubricity when hydrated than when dry.

9. A device for occluding a cavity, the device comprising:

an elongated, filamentous carrier having a looped portion, the carrier being formed of a biocompatible material having an elastic memory and an external surface; and a coaxial member of an expansile hydrogel formed over the carrier such that the member covers a substantial portion of the external surface of the looped portion of the carrier;

wherein the device has at least one of a greater flexibility and a greater lubricity when the hydrogel is hydrated than when the hydrogel is dehydrated.

10. The device of claim 9, wherein an unsupported end of a portion of the device deflects downward under the weight of the portion and relative to an opposite, supported end of the portion about 0.75 in. (19.1 mm) when:

the hydrogel is in a dry state and a horizontal distance between the opposite ends of the portion is more than about 2.25 in. (57.2 mm);

the hydrogel is in a moderately hydrated state and the horizontal length is between about 1.5 in. (38.2 mm) and 2.25 in. (57.2 mm); and, the hydrogel is in a fully hydrated stated and the horizontal length is less than about 1.5 in (38.2 mm).

11. A device for embolizing a body cavity, the device comprising:

an elongated, filamentous carrier with an external surface, at least a portion of the carrier being a looped portion; and a coaxial member of a hydrophilic polymer covering a substantial portion of the external surface of the looped portion of the carrier;

wherein a physical property of the coaxial member in an aqueous environment is a function of time in the environment and a physical parameter of the environment.

12. The device of claim 11, wherein the physical property is at least one of the flexibility and the lubricity of the member, and wherein the physical parameter of the environment is at least one of the temperature and the pH of the environment.

* * * * *